(12) United States Patent
Besko

(10) Patent No.: US 9,610,040 B2
(45) Date of Patent: Apr. 4, 2017

(54) REMANUFACTURED MEDICAL SENSOR WITH FLEXIBLE FARADAY SHIELD

(71) Applicant: COVIDIEN LP, Mansfield, MA (US)

(72) Inventor: David P. Besko, Thornton, CO (US)

(73) Assignee: COVIDIEN LP, Mansfield ( * ) Notice: Subject to any disclaimer, the term of this patent is extended or adjusted under 35 U.S.C. 154(b) by 231 days.

(21) Appl. No.: 14/258,958

(22) Filed: Apr. 22, 2014

(65) Prior Publication Data

US 2014/0228659 A1 Aug. 14, 2014

Related U.S. Application Data

(63) Continuation of application No. 13/239,681, filed on Sep. 22, 2011, now Pat. No. 8,726,496.

(51) Int. Cl.
*H05K 3/36* (2006.01)
*A61B 5/00* (2006.01)
(Continued)

(52) U.S. Cl.
CPC ........ *A61B 5/6833* (2013.01); *A61B 5/02427* (2013.01); *A61B 5/14552* (2013.01);
(Continued)

(58) Field of Classification Search
CPC ............ A61B 5/14552; A61B 5/02427; A61B 5/6833; A61B 5/7203; A61B 2562/182; A61B 2562/222; A61B 2562/12; B32B 37/02; B32B 38/04; B32B 38/145; B32B 2037/268; B32B 2307/202; B32B 2535/00;
(Continued)

(56) References Cited

U.S. PATENT DOCUMENTS

| 4,545,926 A | 10/1985 | Fouts, Jr. et al. |
| 4,621,643 A | 11/1986 | New, Jr. et al. |

(Continued)

FOREIGN PATENT DOCUMENTS

| AU | 2120892 | 4/1993 |
| EP | 0520599 | 12/1992 |

(Continued)

OTHER PUBLICATIONS 3M 1516 Material Safety Data Sheet 3M™ Single Coated Polyester Medical Tape (Mar. 31, 2006).

(Continued)

*Primary Examiner* — Donghai D Nguyen

(57) ABSTRACT

Present embodiments include a remanufactured bandage-type medical sensor having an optical assembly with an emitter adapted to transmit one or more wavelengths of light and a photodetector adapted to receive the one or more wavelengths of light transmitted by the emitter. The sensor also includes a laminate assembly having an electrically conductive adhesive transfer tape (ECATT) layer disposed over the photodetector, and the ECATT layer is adapted to shield the photodetector from electromagnetic interference (EMI). A nonconductive layer supports the emitter, the photodetector, and the ECATT layer within the sensor. At least a portion of the optical assembly is from a used bandage-type medical sensor, and at least a portion of the laminate assembly is new.

15 Claims, 23 Drawing Sheets

(51) Int. Cl.
*A61B 5/1455* (2006.01)
*B32B 37/02* (2006.01)
*A61B 5/024* (2006.01)
*B32B 38/04* (2006.01)
*B32B 38/00* (2006.01)
*B32B 37/26* (2006.01)

(52) U.S. Cl.
CPC ............ *A61B 5/7203* (2013.01); *B32B 37/02* (2013.01); *A61B 2562/12* (2013.01); *A61B 2562/182* (2013.01); *A61B 2562/222* (2013.01); *B32B 38/04* (2013.01); *B32B 38/145* (2013.01); *B32B 2037/268* (2013.01); *B32B 2307/202* (2013.01); *B32B 2307/212* (2013.01); *B32B 2535/00* (2013.01); *Y10T 29/49128* (2015.01); *Y10T 29/49169* (2015.01)

(58) Field of Classification Search
CPC ......... B32B 2307/212; Y10T 29/49128; Y10T 29/49169
USPC ... 29/830–832, 834; 600/310, 323, 344, 372
See application file for complete search history.

(56) References Cited

U.S. PATENT DOCUMENTS

| | | | |
|---|---|---|---|
| 4,862,146 A | 8/1989 | McCoy et al. | |
| 4,964,408 A | 10/1990 | Hink et al. | |
| 5,090,410 A | 2/1992 | Saper et al. | |
| 5,170,786 A | 12/1992 | Thomas et al. | |
| 5,191,292 A | 3/1993 | Klotz et al. | |
| 5,209,230 A | 5/1993 | Swedlow et al. | |
| 5,337,744 A | 8/1994 | Branigan | |
| 5,452,717 A | 9/1995 | Branigan et al. | |
| 5,469,845 A * | 11/1995 | DeLonzor ......... A61B 5/02427 600/372 | |
| 5,491,299 A | 2/1996 | Naylor et al. | |
| 5,595,188 A | 1/1997 | Kassal | |
| 5,660,567 A | 8/1997 | Nierlich et al. | |
| 5,673,693 A | 10/1997 | Solenberger | |
| 5,678,544 A | 10/1997 | DeLonzor et al. | |
| 5,697,367 A * | 12/1997 | Lewis ................ A61B 5/14553 600/310 | |
| 5,752,914 A | 5/1998 | Delonzor et al. | |
| 5,810,724 A | 9/1998 | Gronvall | |
| RE36,000 E | 12/1998 | Swedlow et al. | |
| 5,851,178 A | 12/1998 | Aronow | |
| 5,862,030 A | 1/1999 | Watkins, Jr. et al. | |
| 5,891,026 A | 4/1999 | Wang et al. | |
| 5,910,108 A | 6/1999 | Solenberger | |
| 5,919,133 A | 7/1999 | Taylor et al. | |
| 5,999,834 A | 12/1999 | Wang et al. | |
| 6,073,038 A | 6/2000 | Wang et al. | |
| 6,144,868 A | 11/2000 | Parker | |
| 6,149,481 A | 11/2000 | Wang et al. | |
| 6,225,565 B1 | 5/2001 | Prysner | |
| 6,253,098 B1 | 6/2001 | Walker et al. | |
| 6,256,523 B1 | 7/2001 | Diab et al. | |
| 6,321,100 B1 | 11/2001 | Parker | |
| 6,343,224 B1 | 1/2002 | Parker | |
| 6,377,829 B1 | 4/2002 | Al-Ali | |
| 6,519,487 B1 | 2/2003 | Parker | |
| 6,534,999 B2 | 3/2003 | Brown | |
| 6,653,557 B2 | 11/2003 | Wolf et al. | |
| 6,671,531 B2 | 12/2003 | Al-Ali et al. | |
| 6,678,543 B2 | 1/2004 | Diab et al. | |
| 6,681,126 B2 | 1/2004 | Solenberger | |
| 6,684,091 B2 | 1/2004 | Parker | |
| 6,725,075 B2 | 4/2004 | Al-Ali | |
| 6,735,459 B2 | 5/2004 | Parker | |
| 6,745,061 B1 | 6/2004 | Hicks et al. | |
| 6,748,254 B2 | 6/2004 | O'Neil et al. | |
| 6,773,532 B2 | 8/2004 | Wolf et al. | |
| 6,792,300 B1 | 9/2004 | Diab et al. | |
| 6,813,511 B2 | 11/2004 | Diab et al. | |
| 6,830,549 B2 | 12/2004 | Bui et al. | |
| 6,920,345 B2 | 7/2005 | Al-Ali et al. | |
| 6,950,687 B2 | 9/2005 | Al-Ali | |
| 6,985,764 B2 | 1/2006 | Mason et al. | |
| 7,039,449 B2 | 5/2006 | Al-Ali | |
| 7,047,054 B2 | 5/2006 | Benni | |
| 7,048,687 B1 | 5/2006 | Reuss et al. | |
| 7,225,007 B2 | 5/2007 | Al-Ali et al. | |
| 7,245,953 B1 | 7/2007 | Parker | |
| 7,272,425 B2 | 9/2007 | Al-Ali | |
| 7,280,858 B2 | 10/2007 | Al-Ali et al. | |
| 7,313,427 B2 | 12/2007 | Benni | |
| 7,340,287 B2 | 3/2008 | Mason et al. | |
| 7,418,284 B2 | 8/2008 | DeLonzor et al. | |
| 7,440,788 B2 | 10/2008 | Jenkins et al. | |
| 7,561,905 B2 | 7/2009 | DeLonzor et al. | |
| 7,684,842 B2 | 3/2010 | Ollerdessen | |
| 2003/0171662 A1 | 9/2003 | O'Connor et al. | |
| 2003/0201781 A1 | 10/2003 | McCoy et al. | |
| 2003/0212312 A1 | 11/2003 | Coffin et al. | |
| 2004/0133088 A1 | 7/2004 | Al-Ali | |
| 2004/0147822 A1 | 7/2004 | Al-Ali et al. | |
| 2004/0173368 A1 | 9/2004 | Dickson | |
| 2005/0043600 A1 | 2/2005 | Diab et al. | |
| 2005/0197550 A1 | 9/2005 | Al-Ali | |
| 2006/0081071 A1 | 4/2006 | Kessler et al. | |
| 2006/0200018 A1 | 9/2006 | Al-Ali | |
| 2006/0211924 A1 | 9/2006 | Dalke et al. | |
| 2007/0078311 A1 | 4/2007 | Al-Ali et al. | |
| 2007/0112260 A1 | 5/2007 | Diab et al. | |
| 2007/0123763 A1 | 5/2007 | Al-Ali et al. | |
| 2007/0244378 A1 | 10/2007 | Al-Ali et al. | |
| 2008/0009691 A1 | 1/2008 | Parker | |
| 2008/0015570 A1 | 1/2008 | Ormsby et al. | |
| 2008/0017800 A1 | 1/2008 | Benni | |
| 2008/0033267 A1 | 2/2008 | Al-Ali | |
| 2008/0076982 A1 | 3/2008 | Ollerdessen et al. | |
| 2008/0081492 A1 | 4/2008 | Sawatari et al. | |
| 2008/0081508 A1 | 4/2008 | Sawatari et al. | |
| 2008/0081971 A1 | 4/2008 | Ollerdessen | |
| 2008/0091089 A1 | 4/2008 | Guillory et al. | |
| 2008/0091090 A1 | 4/2008 | Guillory et al. | |
| 2008/0197301 A1 | 8/2008 | Diab | |
| 2008/0208023 A1 | 8/2008 | Gruvac et al. | |
| 2008/0255435 A1 | 10/2008 | Al-Ali et al. | |
| 2008/0275326 A1 | 11/2008 | Kasielke et al. | |
| 2009/0259114 A1 | 10/2009 | Johnson et al. | |
| 2009/0323067 A1 | 12/2009 | Medina | |
| 2009/0323267 A1 | 12/2009 | Besko et al. | |
| 2010/0081902 A1 | 4/2010 | McKenna et al. | |
| 2010/0249554 A1 | 9/2010 | McKenna et al. | |
| 2010/0249557 A1 | 9/2010 | Besko et al. | |
| 2010/0301215 A1 | 12/2010 | Gonopolskiy et al. | |
| 2010/0327063 A1 | 12/2010 | Medina et al. | |
| 2010/0328034 A1 | 12/2010 | Medina et al. | |
| 2011/0009719 A1 | 1/2011 | Al-Ali | |
| 2012/0019475 A1 | 1/2012 | Li et al. | |
| 2012/0071742 A1 | 3/2012 | Medina | |
| 2013/0079609 A1 | 3/2013 | Besko | |
| 2013/0079611 A1 | 3/2013 | Besko | |

FOREIGN PATENT DOCUMENTS

| | | |
|---|---|---|
| EP | 1986543 | 8/2007 |
| EP | 1945099 | 7/2008 |
| JP | 27195816 | 8/2007 |
| KR | 2011-0091261 | 8/2011 |
| WO | WO03058646 | 7/2003 |
| WO | WO2005010568 | 2/2005 |
| WO | WO2007041338 | 4/2007 |
| WO | WO2007097754 | 8/2007 |
| WO | WO2008118216 | 10/2008 |

OTHER PUBLICATIONS 3M 9712 XYZ-Axis Electrically Conductive Tape (Aug. 2001).
3M Technical Bulletin Typical Properties for 3M™ Electrically

(56) References Cited

OTHER PUBLICATIONS

Conductive Adhesive Films (Feb. 2000).
3M™ 9713 XYZ-Axis Electrically Conductive Tape, Apr. 2009.
3M™ EMI/EMC Solutions More Protection More Control—EMI/RFI (2010).
PCT Search Report and Written Opinion for related PCT Application No. PCT/US2012/053011 mailed Feb. 26, 2013, 16 pages.
International Search Report and Written Opinion for PCT Application No. PCT/US2012/053013 dated Aug. 13, 2013, 15 pgs.

* cited by examiner

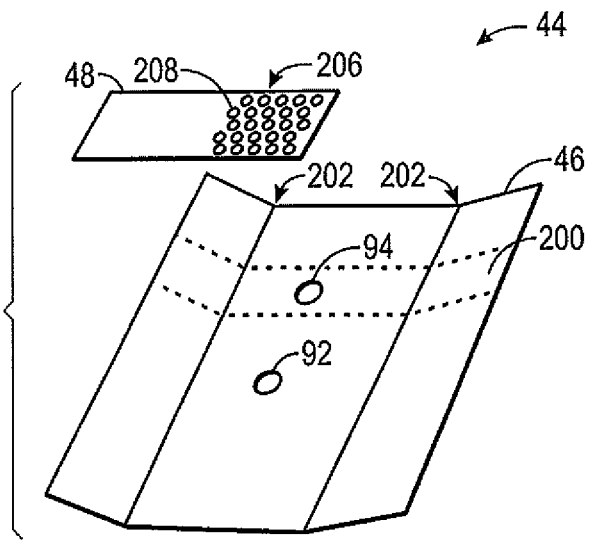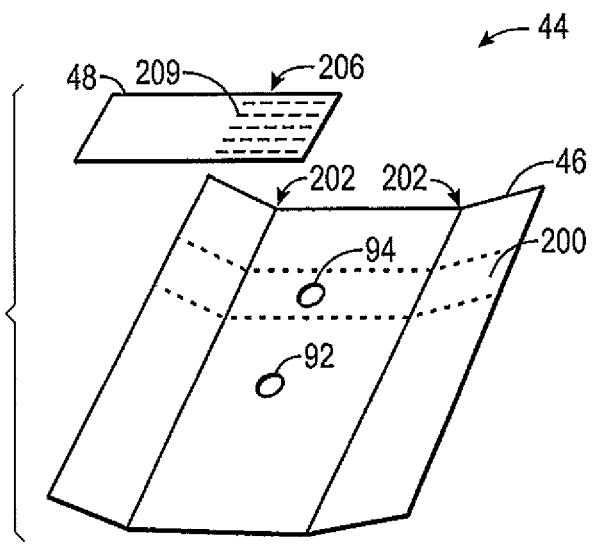

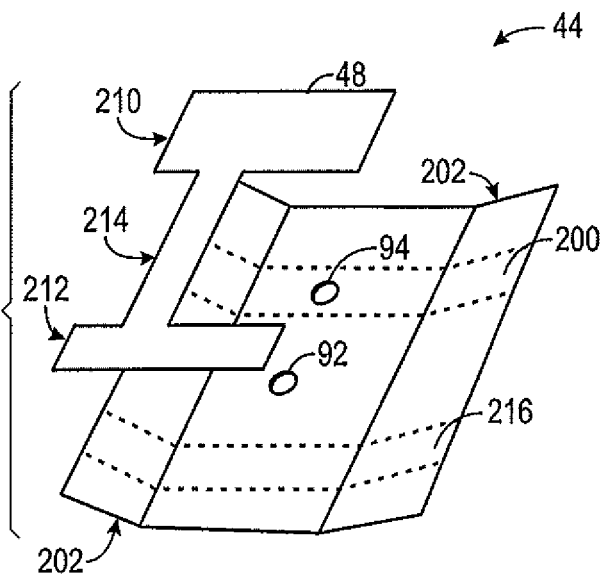
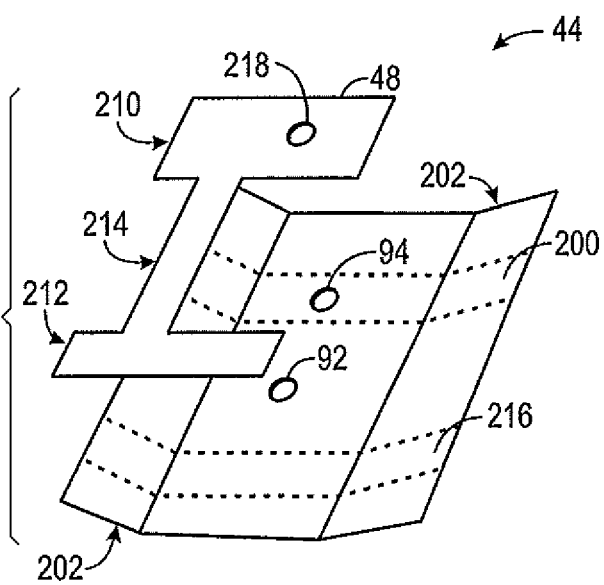

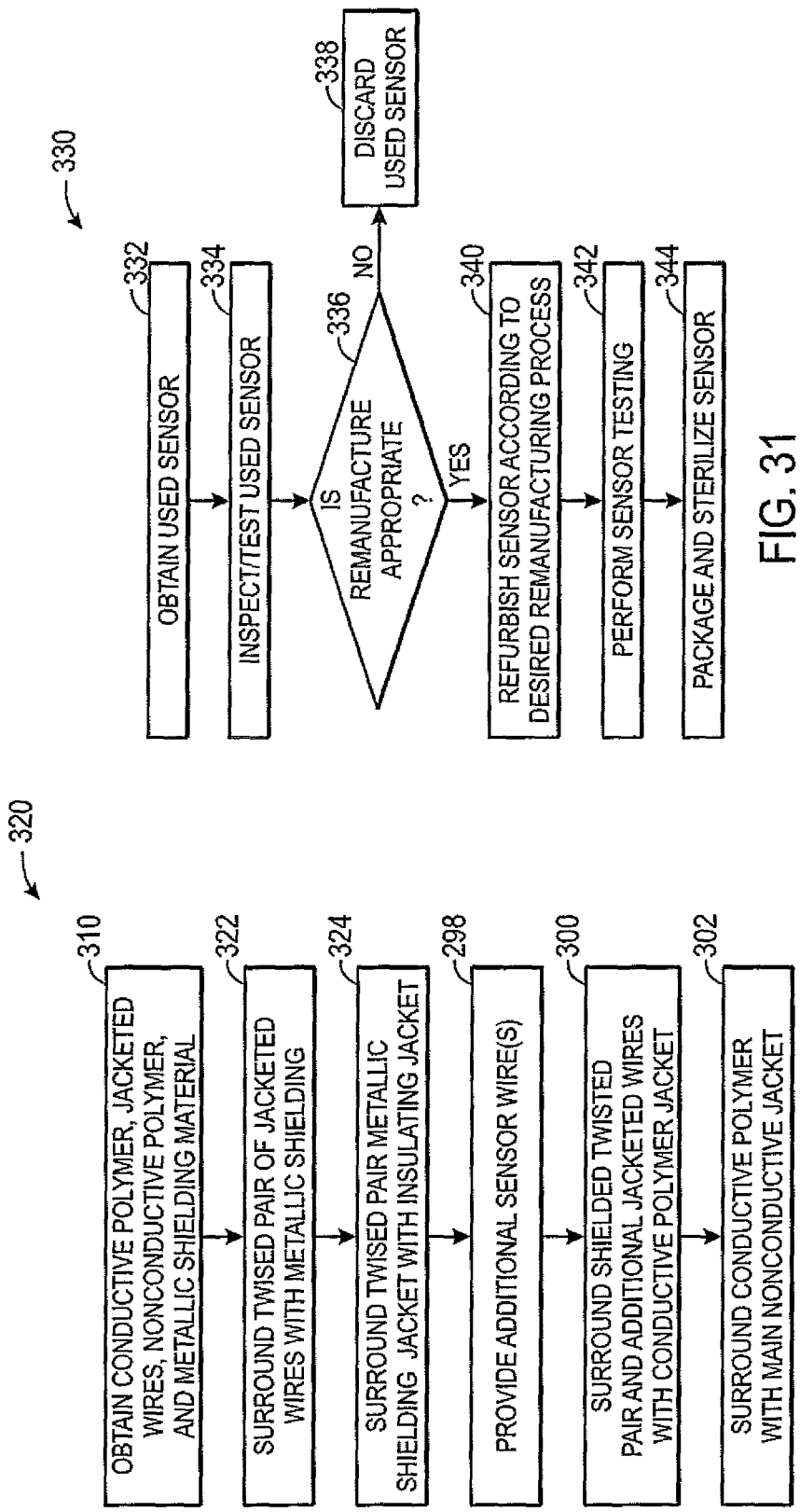

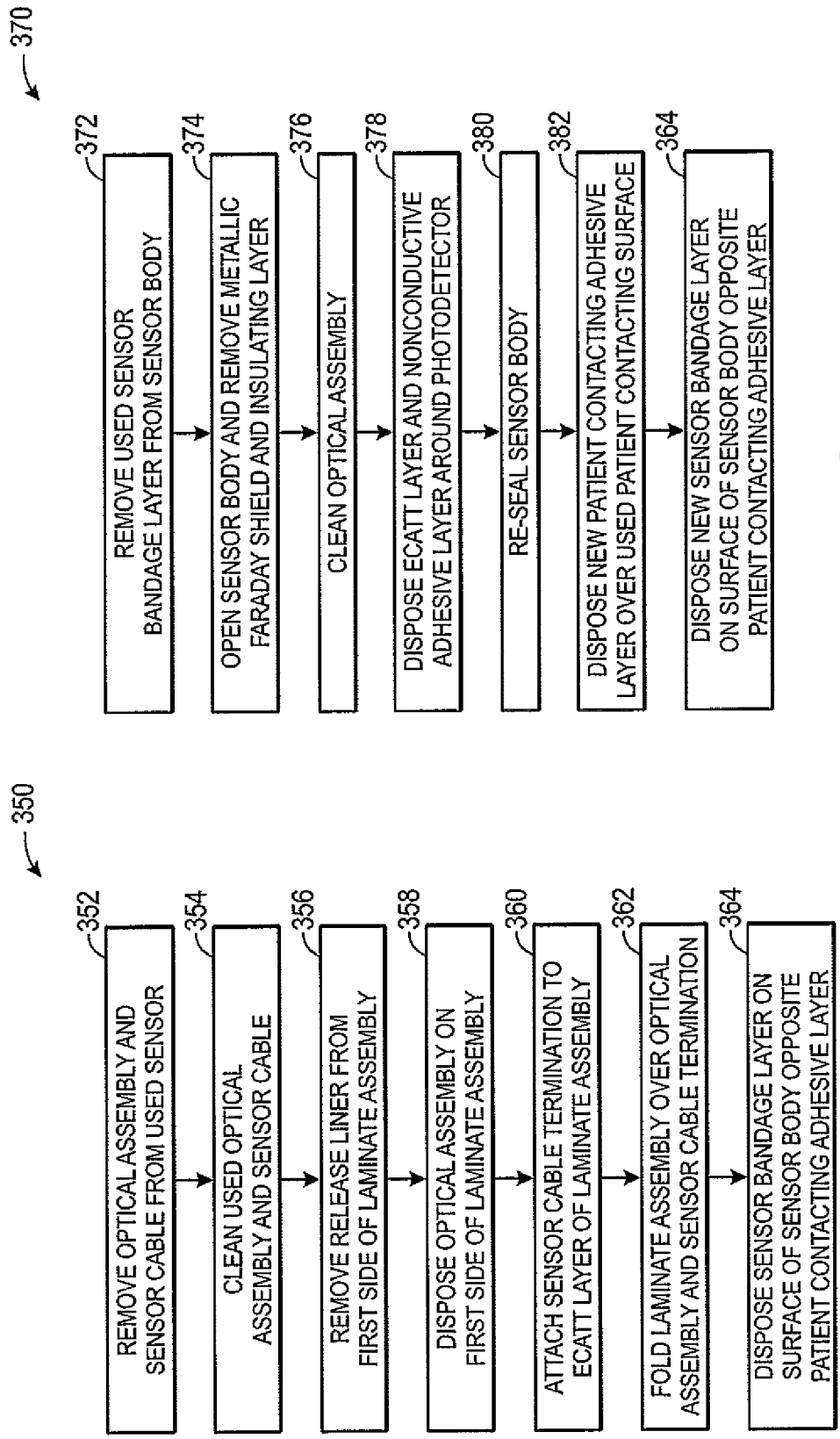

REMANUFACTURED MEDICAL SENSOR WITH FLEXIBLE FARADAY SHIELD

CROSS-REFERENCE TO RELATED APPLICATIONS

This application is a continuation of and claims priority to U.S. patent application Ser. No. 13/239,681, filed on Sep. 22, 2011 and entitled "TECHNIQUE FOR REMANUFACTURING A MEDICAL SENSOR," which is incorporated by reference herein in its entirety for all purposes.

BACKGROUND

The present disclosure relates generally to medical sensors and, more particularly, to the mitigation of electromagnetic interference in such sensors.

This section is intended to introduce the reader to various aspects of art that may be related to various aspects of the present disclosure, which are described and/or claimed below. This discussion is believed to be helpful in providing the reader with background information to facilitate a better understanding of the various aspects of the present disclosure. Accordingly, it should be understood that these statements are to be read in this light, and not as admissions of prior art.

In the field of medicine, doctors often desire to monitor certain physiological characteristics of their patients. Accordingly, a wide variety of devices and techniques have been developed for monitoring physiological characteristics. Such devices and techniques provide doctors and other healthcare personnel with the information they need to provide the best possible healthcare for their patients. As a result, these monitoring devices and techniques have become an indispensable part of modern medicine.

One such monitoring technique is commonly referred to as pulse oximetry. Pulse oximetry may be used to measure various blood flow characteristics, such as the blood-oxygen saturation of hemoglobin in arterial blood and/or the rate of blood pulsations corresponding to each heartbeat of a patient. The devices based upon pulse oximetry techniques are commonly referred to as pulse oximeters. Pulse oximeters typically utilize a non-invasive sensor that is placed on or against a patient's tissue that is well perfused with blood, such as a patient's finger, toe, forehead or earlobe. The pulse oximeter sensor emits light and photoelectrically senses the absorption and/or scattering of the light after passage through the perfused tissue. A photo-plethysmographic waveform, which corresponds to the cyclic attenuation of optical energy through the patient's tissue, may be generated from the detected light. Additionally, one or more physiological characteristics may be calculated based upon the amount of light absorbed or scattered. More specifically, the light passed through the tissue may be selected to be of one or more wavelengths that may be absorbed or scattered by the blood in an amount correlative to the amount of the blood constituent present in the blood. The amount of light absorbed and/or scattered may then be used to estimate the amount of blood constituent in the tissue using various algorithms.

For example, a reflectance-type sensor placed on a patient's forehead may emit light into the skin and detect the light that is "reflected" back after being transmitted through the forehead tissue. A transmission-type sensor having a bandage configuration may be placed on a finger, wherein the light waves are emitted through and detected on the opposite side of the finger. In either case, the amount of light detected may provide information that corresponds to valuable physiological patient data. The data collected by the sensor may be used to calculate one or more of the above physiological characteristics based upon the absorption or scattering of the light. For instance, the emitted light is typically selected to be of one or more wavelengths that are absorbed or scattered in an amount related to the presence of oxygenated versus de-oxygenated hemoglobin in the blood. The amount of light absorbed and/or scattered may be used to estimate the amount of the oxygen in the tissue using various algorithms.

The sensors generally include an emitter that emits the light and a detector that detects the light. The emitter and detector may be located on a flexible circuit that allows the sensor to conform to the appropriate site on the patient's skin, thereby making the procedure more comfortable for a patient. During use, the emitter and detector may be held against the patient's skin to facilitate the transmission of light through the skin of the patient. For example, a sensor may be folded about a patient's finger tip with the emitter placed proximate and/or against the finger nail, and the detector placed against the under side of the finger tip. When fitted to the patient, the emitted light may travel directly through the tissue of the finger and be detected without additional light being introduced or the emitted light being scattered.

The quality and reproducibility of these measurements may depend on a number of factors. The detector and emitter may include materials to protect measurement signals from being affected by external static electrical fields, external light, electromagnetic interference (EMI), radio frequency interference (RFT), or the like. For example, the detector may be covered by a metallic Faraday shield to prevent EMI from interfering with measurement signals produced at the detector. Similarly, wiring connected to the emitter and the detector (e.g., for transmitting power and/or signals) may be surrounded by metallic shielding to prevent EMI from interfering with transmitted measurement signals, and to prevent crosstalk between wiring. Unfortunately, these materials can add to the bulkiness and inflexibility of the sensor, which may be uncomfortable for a patient. Additionally, these shielding materials may be subject to degradation or breakage, which can result in a loss of overall shielding efficiency.

SUMMARY

A summary of certain embodiments disclosed herein is set forth below. It should be understood that these aspects are presented merely to provide the reader with a brief summary of these certain embodiments and that these aspects are not intended to limit the scope of this disclosure. Indeed, this disclosure may encompass a variety of aspects that may not be set forth below.

Embodiments of the present disclosure relate to the use of flexible electrically conductive materials within medical sensors and cables to which medical sensors and devices may be connected. These conductive materials are adapted to act as Faraday shields for the mitigation of RFI and EMI in various circuitry and/or electrical leads of the sensor and cable. For example, a bandage sensor may include a laminated sensor body having several layers. One layer may be an electrically conductive adhesive transfer tape (ECATT) layer disposed about a detector of the sensor to reduce EMURFI. The ECATT layer may be used in lieu of a fully metallic (e.g., copper) Faraday shield, providing enhanced conformance to a patient. As another example, a cable, such as a sensor cable, may incorporate one or more conductive polymers extruded or otherwise disposed over one or more wires of the cable, such as the wires that carry the emitter and/or the detector signals. The conductive polymers may be used in lieu of certain metallic shielding jackets, thereby providing enhanced flexibility and EMI/RFI shielding for the cable.

Certain embodiments of the present disclosure relate to methods of remanufacturing used sensors and cables to produce sensors and cables having the disclosed materials, or to remove the disclosed materials from the sensors and cables. For example, various components of a used bandage sensor may be retained and incorporated into a new bandage sensor having an ECATT layer as a Faraday shield. Similarly, various components of a used sensor cable may be retained and used to construct a new sensor cable having a conductive polymeric jacket disposed over one or more wires for EMI/RFI shielding.

BRIEF DESCRIPTION OF THE DRAWINGS

Advantages of the disclosed techniques may become apparent upon reading the following detailed description and upon reference to the drawings in which:

FIG. 14 is an exploded perspective view of an embodiment of an electrically conductive adhesive transfer tape layer and a main nonconductive support layer, the electrically conductive adhesive transfer tape layer having an optical grid, in accordance with an embodiment of the present disclosure;

FIG. 15 is an exploded perspective view of an embodiment of an electrically conductive adhesive transfer tape layer and a main nonconductive support layer, the electrically conductive adhesive transfer tape layer having an optical grid, in accordance with an embodiment of the present disclosure;

FIG. 16 is an exploded perspective view of an embodiment of an electrically conductive adhesive transfer tape layer and a main nonconductive support layer, the electrically conductive adhesive transfer tape layer having a detector-shielding section, a cable termination section, and a grounding section, in accordance with an embodiment of the present disclosure;

FIG. 17 is an exploded perspective view of an embodiment of an electrically conductive adhesive transfer tape layer and a main nonconductive support layer, the electrically conductive adhesive transfer tape layer having a detector-shielding section, a cable termination section, a grounding section, and an optical window in the detector-shielding section, in accordance with an embodiment of the present disclosure;

FIG. 30 is a process flow diagram illustrating an embodiment of a method for producing the sensor cable of FIG. 29, in accordance with an aspect of the present disclosure;

FIG. 31 is a process flow diagram illustrating an embodiment of a general method for remanufacturing a medical sensor, in accordance with an aspect of the present disclosure;

FIG. 32 is a process flow diagram illustrating an embodiment of a method for remanufacturing a bandage sensor to include the laminate assembly of FIG. 4, in accordance with an aspect of the present disclosure;

FIG. 33 is a process flow diagram illustrating an embodiment of a method for remanufacturing a bandage sensor in a manner that replaces a fully metallic Faraday shield with an electrically conductive adhesive transfer tape layer, in accordance with an aspect of the present disclosure;

DETAILED DESCRIPTION OF SPECIFIC EMBODIMENTS

Figure 1:
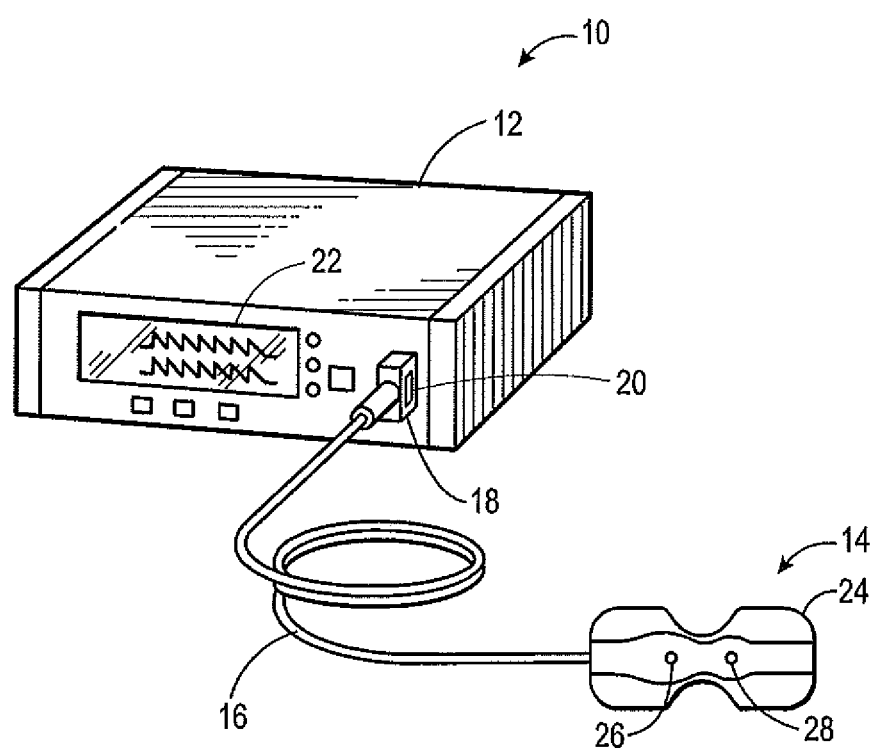
FIG. 1 is a perspective view of a medical sensor system having a bandage sensor with a flexible Faraday shield, in accordance with an embodiment of the present disclosure.

One or more specific embodiments of the present techniques will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present disclosure, the articles "a," "an," and "the" are intended to mean that there are one or more of the elements. The terms "comprising," "including," and "having" are intended to be inclusive and mean that there may be additional elements other than the listed elements. Additionally, it should be understood that references to "one embodiment" or "an embodiment" of the present disclosure are not intended to be interpreted as excluding the existence of additional embodiments that also incorporate the recited features. Also, as used herein, the term "over" or "above" refers to a component location on a sensor that is closer to patient tissue when the sensor is applied to the patient. For example, a bandage portion of a bandage sensor may be understood to be "over" or "above" the emitter or detector of the sensor, as will be described below.

As noted above, the present embodiments relate to bandage sensors and cables (e.g., sensor cables) incorporating ECATT layers and/or electrically conductive polymers for EMI/RFI shielding. For example, the ECATT layers and/or the electrically conductive polymers may be adapted to serve as Faraday shields. Such bandage sensors and cables may be entirely constructed from new materials (i.e., materials that have not been incorporated into a medical sensor), or may be constructed using some new components as well as components taken from one or more used sensors. For example, a bandage sensor may include an adhesive bandage portion disposed over a laminated body housing various electronic components. The adhesive bandage portion and the laminated body may be configured to wrap around a digit (e.g., a finger or a toe) of a patient. By way of example, the MAX-A™ pulse oximeter sensor or another OXI-MAXT™ sensor by Nellcor Puritan Bennett LLC represents one such bandage sensor, but other types of sensors, such as those used for measuring water fraction, hematocrit, BIS, etc., may benefit from the techniques disclosed herein as well. An example system incorporating such a bandage sensor is discussed with respect to FIG. 1, with various features of the bandage sensor, such as the ECATT Faraday shield, being discussed with respect to FIGS. 2-4.

These bandage sensors are generally known to be one-time-use medical sensors that may be disposed after use by one patient. Though disposable, some components of these used bandage sensors and the cables associated therewith may be employed in the construction of bandage sensors incorporating various features disclosed herein, such as an ECATT layer and/or an electrically conductive polymer. Example methods for making bandage sensors from new and/or used components are discussed with respect to FIGS. 5-23 and 31-36. Indeed, as discussed in greater detail below, such components may include, for example, a cable, an emitter and detector, and, in some embodiments, various layers that surround the emitter and detector. Reusing such components to reconstruct a bandage sensor may reduce waste, consequently reducing an impact on the environment, while accordingly reducing costs. Additionally, certain components may be removed to increase the flexibility and conformance of the resulting sensor. For example, a used bandage sensor having a fully metallic Faraday shield may be remanufactured to have a more flexible Faraday shield formed from an ECATT layer. Similarly, a cable having a fully metallic wire jacket for EMI/RFI protection may be manufactured and/or remanufactured to include a conductive polymer jacket in the place of a metallic jacket. Such embodiments are discussed with respect to FIGS. 24-30, 37, and 39-41.

With the foregoing in mind, FIG. 1 illustrates a perspective view of an embodiment of a non-invasive medical sensor system 10 having an electronic patient monitor 12 and a bandage sensor 14 having a Faraday shield constructed from an electrically conductive adhesive transfer tape. By way of example, the patient monitor 12 may be a patient monitor by Nellcor™ or another manufacturer. In some embodiments, the bandage sensor 14 may be remanufactured, as discussed below, from new components and components of a bandage sensor that has been used and/or discarded. The patient monitor 12 may exchange signals with the bandage sensor 14 via a sensor cable 16 having one or more electrically conductive polymeric wire jackets for EMI/RFI protection. The sensor cable 16 may interface with the patient monitor 12 via a connector 18, which may include a memory module 20 configured to store sensor-specific data, such as calibration coefficients, as well as patient historical information (e.g., an alarm history). The memory module 20 may also communicate information, such as troubleshooting information, to a caregiver through the patient monitor 12.

The patient monitor 12 may include a display 22 for providing information to the caregiver, as well as various monitoring and control features. In certain embodiments, the patient monitor 12 may include a processor that may determine a physiological parameter of a patient based on these signals obtained from the bandage sensor 14. Indeed, in the presently illustrated embodiment of the system 10, the bandage sensor 14 is a pulse oximetry sensor that noninvasively obtains pulse oximetry data from a patient.

The bandage sensor 14 may include a bandage portion 24 that facilitates attachment to pulsatile patient tissue (e.g., a patient's digit). An emitter 26 and a detector 28 may operate to generate non-invasive pulse oximetry data for use by the patient monitor 12. In particular, the emitter 26 may transmit light at certain wavelengths (e.g., infrared (IR), near-IR) into the tissue and the detector 28 may receive the light after it has passed through or is reflected by the tissue. The amount of light and/or certain characteristics of light waves passing through or reflected by the tissue may vary in accordance with changing amounts of blood contingents in the tissue, as well as related light absorption and/or scattering.

The emitter 26 may emit light from one or more light emitting diodes (LEDs) or other suitable light sources into the pulsatile tissue. The light that is reflected or transmitted through the tissue may be detected using the detector 28, which may be a photodetector (e.g., a photodiode). When the detector 28 detects this light, the detector 28 may generate a photocurrent proportional to the amount of detected light, which may be transmitted through the sensor cable 16 to the patient monitor 12. The patient monitor 12 may convert the photocurrent from the detector 28 into a voltage signal that may be analyzed to determine certain physiological characteristics of the patient.

To protect these signals (e.g., the photocurrent) from interference, such as electromagnetic interference, the bandage sensor 14 and sensor cable 16, as noted above, may include features for EMI/RFI shielding. As an example, these shielding features may include a Faraday shield disposed over the detector 28 of the bandage sensor 14 and a conductive jacketing material disposed over one or more electrical wires of the sensor cable 16. Further, to enhance the conformance of the bandage sensor 14 to the pulsatile patient tissue, the shielding features may be constructed from materials that afford enhanced flexibility compared to fully metallic Faraday shields and fully metallic wire jackets. The enhanced flexibility of the resulting bandage sensor 14 may facilitate the proper placement of the optics with respect to the monitored tissue and may also enhance patient comfort.

Figure 2:
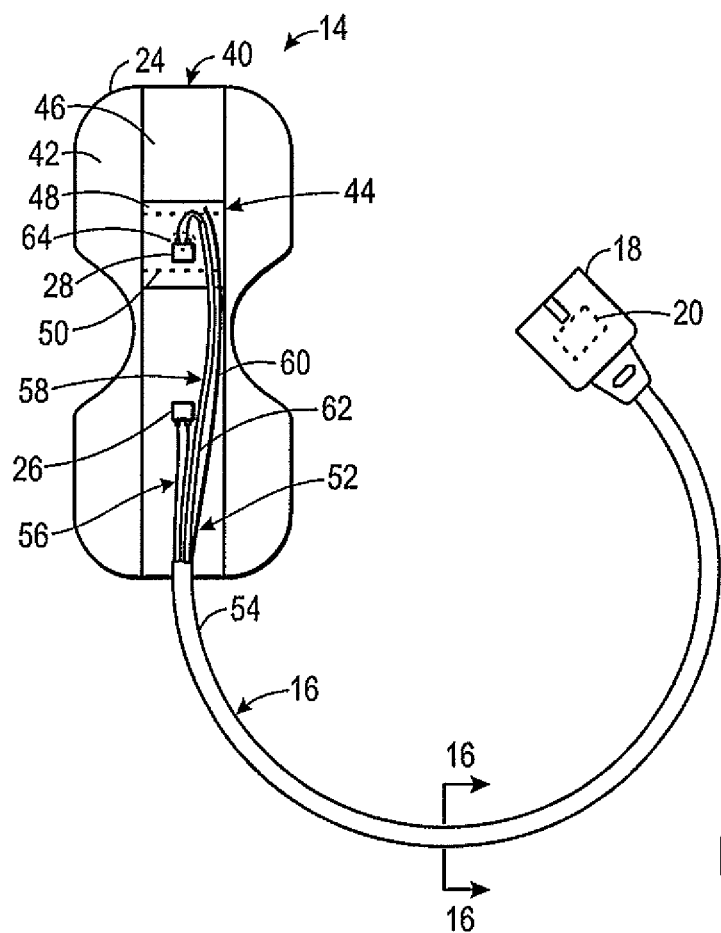
FIG. 2 is a cut away top view of the bandage sensor of FIG. 1 having an electrically conductive adhesive transfer tape layer as a Faraday shield for the detector, in accordance with an embodiment of the present disclosure.

For example, turning to FIG. 2, which is an internal view of the bandage sensor 14, a flexible sensor body 40 is illustrated as disposed over a patient-contacting surface 42 of the bandage portion 24. The sensor body 40 may include a laminate assembly 44, the emitter 26, and the detector 28. The laminate assembly 44 may generally include a plurality of flexible layers. The flexible layers, in the illustrated embodiment, include a main nonconductive support layer 46, a flexible, electrically conductive adhesive transfer tape (ECATT) layer 48, and a nonconductive adhesive layer 50. The composition of each of the layers 46, 48, and 50 is discussed in further detail below with respect to FIG. 4. Generally, the laminate assembly 44 surrounds the emitter 26 and the detector 28 when the bandage sensor 14 is assembled. The laminate assembly 44 also surrounds a plurality of wires 52, some of which provide power to and carry signals from the emitter 26 and/or the detector 28. The plurality of wires 52 may extend from a main jacket 54 of the sensor cable 16 as the wires 52 enter the sensor body 40 and connect to the emitter 26 or the detector 28.

The plurality of wires 52 may include a first pair of wires 56 that attach to the emitter 26, a second pair of wires 58 that attach to the detector 28, and a drain wire 60 that terminates the sensor cable 16 and also provides a ground for the ECATT layer 48. The first pair of wires 56 may enter the sensor body 40 independent of each other, and may each be jacketed with a nonconductive coating, such as a nonconductive polymeric coating. As an example, in embodiments where the emitter 26 includes one or more light emitting diodes (LEDs), the first pair of wires 56 may place an electrical bias across the LED of the emitter 26 to cause light emission. The second pair of wires 58 enter the sensor body 40 as a twisted and jacketed pair. As an example, the second pair of wires 58 may provide power to the detector 28 and/or may carry electrical signals produced by the detector 28 in response to absorbing photons transmitted by the emitter 26. In some embodiments, a jacket 62 covering the twisted, second pair of wires 58 may be adapted to provide electrical insulation within at least a portion of the sensor body 40 and/or the sensor cable 16. Further, as discussed in detail below with respect to FIGS. 24-29, the second pair of wires 58 may be jacketed in a conductive polymer material rather than a metallic jacket (e.g., a fully metallic jacket) so as to provide EMI/RFI shielding with enhanced flexibility.

The second pair of wires 58 may connect to the detector 28 at a connection area 64, where the second pair of wires 58 are left exposed (e.g., not covered by a jacket). Accordingly, the second pair of wires 58 may be susceptible to EMI/RFI at the connection area 64. Therefore, in some embodiments, in addition to covering the detector 28, the ECATT layer 48 may cover the second pair of wires 58 at least at the connection area 64. Specifically, in some embodiments, the detector 28 and the connection area 64 may be covered by and in direct contact with the nonconductive adhesive layer 50, with the ECATT layer 48 being disposed over the nonconductive adhesive layer 50. The drain wire 60, as noted above, may dissipate the EMI/RFI that is blocked by the ECATT layer 48. Advantageously, the ECATT layer 48 and the drain wire 60, during assembly of the bandage sensor 14, may be connected to one another by the pressure-sensitive adhesive of the ECATT layer 48, rather than via a solder as in fully metallic Faraday shields. Indeed, the elimination of such a step may advantageously increase throughput during the manufacture of the bandage sensor 14.

For example, when the bandage sensor 14 is assembled, the emitter 26, the detector 28, and the plurality of wires 52 may be placed over the laminate assembly 44 in their respective positions. The laminate assembly 44 may be folded over the emitter 26, the detector 28, and the plurality of wires 52 to form the sensor body 40. By folding the laminate assembly 44 in this manner, the ECATT layer 48 and the nonconductive adhesive layer 50 provide substantially 360° EMI/RFI protection of the detector 28 and the connection area 64. Additionally, the folded ECATT layer 48 may form a substantially 360° termination for the drain wire 60. To form the bandage sensor 14 after the sensor body 40 has been assembled, the bandage portion 24 of the sensor is placed on the sensor body 40, as illustrated in FIG. 3.

Figure 3:
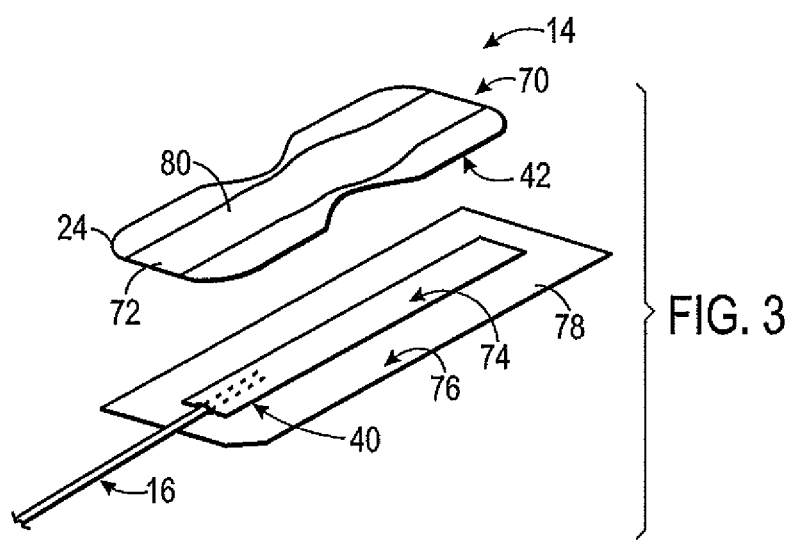
FIG. 3 is an exploded perspective view of the bandage sensor of FIGS. 1 and 2 illustrating a bandage top assembly as exploded away from a sensor body of the bandage sensor, in accordance with an embodiment of the present disclosure.

In FIG. 3, a bandage top assembly 70 of the bandage sensor is illustrated as exploded away from the sensor body 40. In the illustrated embodiment, the bandage top assembly 70 includes the bandage portion 24 and a metallic layer 72 (e.g., an aluminized layer). When the bandage sensor 14 is produced, the bandage top assembly 70 may be laminated on top of the sensor body 40. Specifically, the bandage top assembly 70 may be laminated on the sensor body 40 such that the metallic layer 72 covers the sensor body 40, with the remaining portion of the bandage top assembly 70 being laminated against a surface 76 of a bottom release liner 78. Lamination of the metallic layer 72 over the sensor body 40 may enable the metallic layer 72 to block the transmission of ambient light into the sensor body 40. In some embodiments, the metallic layer 72 may also have an opaque ink printed on an outward-facing surface 80 to provide enhanced optical insulation for the sensor body 40 and to limit reflectance. Further, the lamination of the bandage portion 24 of the bandage top assembly 70 against the bottom release liner 78 may protect the patient-contacting surface 42 from inadvertent contact prior to use.

Figure 4:
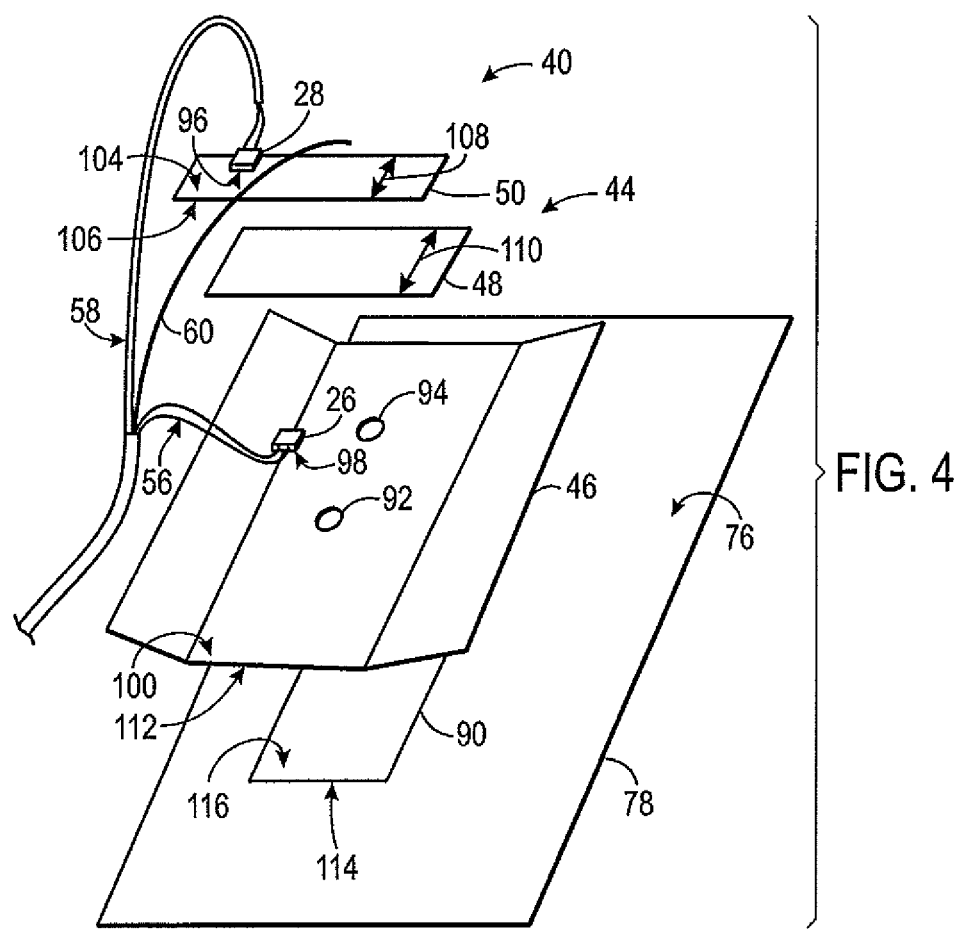
FIG. 4 is an exploded perspective view of the bandage sensor of FIG. 2 illustrating the optics of the bandage sensor and a laminate assembly of the bandage sensor as exploded away from one another, in accordance with an embodiment of the present disclosure.

Before the bandage top assembly 70 is laminated on the sensor body 40 to form the bandage sensor 14, the sensor body 40 may be constructed by placing the emitter 26 and the detector 28 on discrete locations of the laminate assembly 44. One embodiment of the layers that form the laminate assembly 44 and the positioning of the emitter 26 and the detector 28 relative to the laminate assembly 44 is depicted in FIG. 4. As illustrated, the laminate assembly 44 includes the main nonconductive support layer 46, the ECATT layer 48, the nonconductive adhesive layer 50, a patient-contacting adhesive layer 90, and the bottom release liner 78.

The main nonconductive support layer 46 supports the laminate assembly 44, the emitter 26, the detector 28, and the plurality of wires 52 within the sensor body 40. The main nonconductive support layer 46 may be constructed from any flexible polymeric or similar material that is approved or qualified for medical use and is capable of supporting various sensor components. Generally, the main nonconductive support layer 46 will be constructed from a polymeric material that is substantially non-transparent (i.e., opaque) with respect to wavelengths of light that may interfere with the measurements performed by the bandage sensor 14. As an example, the main nonconductive support layer 46 may be constructed from an opaque (e.g., white) polypropylene that blocks wavelengths of light that may be used for pulse oximetry, such as infrared, near-infrared, visible, ultraviolet, or any combination thereof (e.g., between approximately 600 and 1400 nm).

Because the main nonconductive support layer 46 is non-transparent with respect to the wavelengths emitted by the emitter 26 and received by the detector 28, the main nonconductive support layer 46 includes a first optical window 92 and a second optical window 94. The first optical window 92 is adapted to allow the emitter 26 to emit wavelengths of light toward the pulsatile patient tissue, and the second optical window 94 is adapted to allow the detector 28 to receive the light transmitted through the tissue from the emitter 26. Indeed, as illustrated, an active face 96 of the detector 28 faces the second optical window 94 and an active face 98 of the emitter 26 faces the first optical window 92.

The emitter 26 and the detector 28 are oriented toward a first surface 100 of the main nonconductive support layer 46. In some embodiments, the first surface 100 may have a pressure-sensitive adhesive to facilitate lamination and placement of various sensor components. The ECATT layer 48, which is laminated on a portion of the first surface 100, may be any transfer tape (i.e., a tape layer having an adhesive disposed on both sides) having a suitable amount of electrical conductivity. The suitable amount of electrical conductivity of the ECATT layer 48 may enable the ECATT layer 48 to act as a Faraday shield for the detector 28 and to provide a termination for the sensor cable 16. Further, the ECATT layer 48 may be capable of conducting electricity in either or both of the plane of the adhesive and/or the thickness of the adhesive (i.e., in the X and Y planes and/or along the Z-axis).

For example, in some embodiments, the adhesive of the ECATT layer 48 may be a pressure-sensitive adhesive (e.g., an acrylic adhesive) having a conductive filler material. The conductive filler material may include any conductive filler, such as beads (e.g., polymeric, solid oxide, semi-metallic, or metallic beads) that may be metal-coated, fibers (e.g., polymeric, solid oxide, metallic, semi-metallic, or carbon fibers) that may be metal-coated, particles (e.g., polymeric, solid oxide, semi-metallic, or metallic particles) that may be metal-coated, or any combination thereof. In some embodiments, the ECATT layer 48 may be 3M™ 9713 XYZ-axis electrically conductive tape or 3M™ 9712 XYZ-axis electrically conductive tape, which are available from 3M Company of St. Paul, Minn. The ECATT layer 48, depending at least on the nature of its adhesive material (e.g., the conductive filler material and/or the pressure-sensitive adhesive), may be substantially transparent or substantially non-transparent with respect to the desired wavelengths of light received by the detector 28.

In embodiments where the ECATT layer 48 is substantially transparent with respect to such wavelengths, the ECATT layer 48 may be laminated on the main nonconductive support layer 46 without forming an optical window in the ECATT layer 48 for the detector 28. For example, in embodiments where the ECATT layer 48 is 3M™ 9713 electrically conductive tape, the ECATT layer 48 may be laminated on the main nonconductive support layer 46 without forming an optical window in the ECATT layer 48. Conversely, in embodiments where the ECATT layer 48 is substantially non-transparent with respect to the wavelengths of light received by the detector 28, at least one optical window may be formed in the ECATT layer 48 prior to or after laminating the ECATT layer 48 on the main nonconductive support layer 46. For example, in embodiments where the ECATT layer 48 is 3M™ 9712 electrically conductive tape, an optical window for the detector 28 may be formed before laminating the ECATT layer 48 on the main nonconductive support layer 46. In other embodiments, an optical window in the ECATT layer 48 may be formed in conjunction with forming the first and second optical windows 92, 94 in the main nonconductive support layer 46. Such embodiments are described in further detail below with respect to FIGS. 5-17.

To insulate the detector 28 from the electrical conductivity of the ECATT layer 48, the nonconductive adhesive layer 50 is laminated on the ECATT layer 48 between the ECATT layer 48 and the detector 28. Further, because the nonconductive adhesive layer 50 may cover the active face 96 of the detector 28, it may be desirable for the nonconductive adhesive layer 50 to be transparent or clear with respect to the desired wavelengths of light received by the detector 28. Accordingly, the nonconductive adhesive layer 50 may include a transparent adhesive disposed on a transparent flexible material, such as a polymer. For example, the nonconductive adhesive layer 50 may have a first side 104 facing the detector 28 and a second side 106 facing the ECATT layer 48. At least the first side 104 may include an adhesive, such as a clear, pressure-sensitive acrylate adhesive, while the second side 106 may have an adhesive or may be substantially free of adhesive. The polymer on which the adhesive is disposed may be any transparent polymer, such as a transparent polyolefin, polyester, or similar polymer. In one embodiment, the nonconductive adhesive layer 50 may be a layer of 3M™ 1516 single-coated polyester medical tape available from 3M Company of St. Paul, Minn.

As noted above, the nonconductive adhesive layer 50 insulates the detector 28, but the drain wire 60 (or other termination feature of the sensor cable 16) terminates via an electrical connection with the ECATT layer 48. Therefore, while the nonconductive adhesive layer 50 may be sized so as to fully insulate the detector 28, a length 108 of the nonconductive adhesive layer 50 may be shorter than a length 110 of the ECATT layer 48 to allow a portion of the ECATT layer 48 to be exposed. That is, a portion of the ECATT layer 48 that is not covered by the nonconductive adhesive layer 50 may be used to terminate the sensor cable 16.

As noted above, the ECATT layer 48, the nonconductive adhesive layer 50, and various internals of the sensor body 40 are provided on the first surface of the main nonconductive support layer 46. Conversely, the patient-contacting adhesive layer 90 and the bottom release liner 78 are provided on a second surface 112 of the main nonconductive support layer 46. The patient-contacting adhesive layer 90 may be a double-sided adhesive layer having a patient-contacting surface 114 and a non-patient contacting surface 116. Further, because the patient-contacting adhesive layer 90 covers the first and second optical windows 92, 94, the patient-contacting adhesive layer 90 may be transparent with respect to the wavelengths that are used for the particular implementation of the bandage sensor 14. As an example, the patient-contacting adhesive layer 90 may be a polymer with a pressure-sensitive acrylic adhesive, such as a double-coated polyethylene layer. The bottom release liner 78, which may be constructed from any suitable release liner material, protects the patient-contacting surface 114 of the patient-contacting adhesive layer 90 from debris and inadvertent attachment prior to the intended use of the bandage sensor 14.

Figure 5:
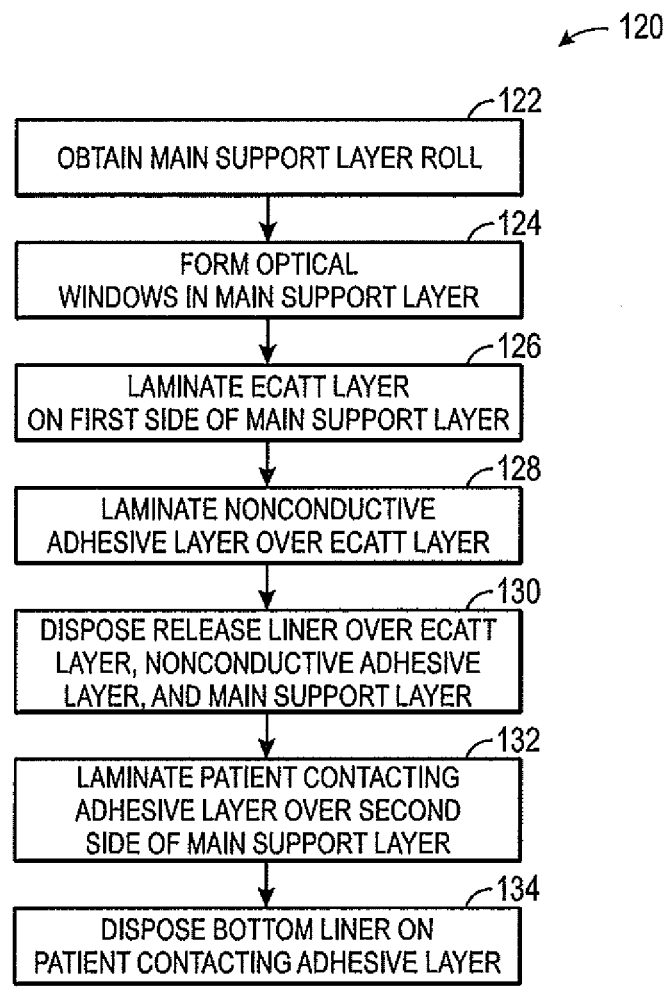
FIG. 5 is a process flow diagram illustrating an embodiment of a method for producing a laminate assembly for inclusion in a bandage sensor, in accordance with an embodiment of the present disclosure.

Using some or all of the materials described above, laminate assemblies in accordance with the present disclosure may be formed singularly or as a roll of laminated layers. Indeed, the present embodiments provide methods for producing laminated rolls that may be used to construct bandage sensors 14 in accordance with the present techniques. FIG. 5 is a process flow diagram depicting an embodiment of one such method 120 for producing a roll having a plurality of laminate assemblies 44. It should be noted that while the steps of method 120 are illustrated in an order, that certain of the steps may be performed in an order that does not follow the illustrated sequence. For example, certain layers may be laminated before, in conjunction with, or after other layers in a manner that produces the laminate assembly 44 discussed herein. In the illustrated embodiment, the method 120 begins with obtaining a roll of the main nonconductive support layer 46 (block 122), which may be a roll of polypropylene or a similar polymer. As noted above, the main nonconductive support layer 46 may have one or more adhesive sides.

After the roll has been obtained in accordance with block 122, the roll of the material of the main nonconductive support layer 46 is pulled and optical windows are formed in the main nonconductive support layer 46 (block 124). For example, the roll may be partially unwound and the first and second optical windows 92, 94 may be formed in the layer 46 by a die cut or a similar procedure. As is discussed in detail below with respect to FIG. 6, the first and second optical windows 92, 94 may be formed across the width of the roll or down the length of the roll.

Upon forming the optical windows in accordance with block 124, the ECATT layer 48 is laminated on the main nonconductive support layer roll (block 126). For example, with reference to FIG. 4, the ECATT layer 48 may be laminated over the first side 100 and over the second optical window 94 of the roll of the main nonconductive support layer 46. In some embodiments, the ECATT layer 48 may be transparent with respect to the wavelengths of interest that may be received by the detector 28. Accordingly, no optical windows may be formed in the ECATT layer 48. Embodiments where an optical window may be formed in the ECATT layer 48 are discussed in further detail below with respect to FIG. 7.

After the ECATT layer 48 is laminated on the main nonconductive support layer 46, the nonconductive adhesive layer 50 may be laminated on the ECATT layer 48 (block 128). However, in other embodiments, the nonconductive adhesive layer 50 may be laminated on the ECATT layer 48 prior to performing the acts represented by block 126. That is, in certain embodiments, the acts represented by block 128 may be performed before or after the acts represented by block 126. In either order, as noted above, the nonconductive adhesive layer 50 may be laminated on the ECATT layer 48 so as to prevent the detector 28 from contacting the ECATT layer 48.

Once the main nonconductive support layer 46, the ECATT layer 48, and the nonconductive adhesive layer 50 have been laminated together in accordance with blocks 124-128, a release liner may be disposed on the layers (block 130). For example, a top release liner may be disposed over the layers to protect the exposed adhesives of the main nonconductive support layer 46, the ECATT layer 48, and the nonconductive adhesive layer 50 prior to their use in assembling the bandage sensor 14.

Before, after, or in conjunction with disposing the release liner over the main nonconductive support layer 46, the ECATT layer 48, and the nonconductive adhesive layer 50 in accordance with block 124, the patient-contacting adhesive layer 90 may be laminated on the second side 112 of the main nonconductive support layer 46 (block 132). For example, as the main nonconductive support layer 46 is unwound in accordance with certain of the acts represented by block 124, the second side 112 may be exposed. Therefore, the patient-contacting adhesive layer 90 may be laminated on the main nonconductive support layer 46 at any point after the acts represented by block 124 are performed. In the illustrated embodiment, however, the patient-contacting adhesive layer 90 may be laminated on the second side 112 of the main nonconductive support layer 46 after the release liner is disposed over the layers on the first side 100 of the main nonconductive support layer 46.

After the ECATT layer 48, the nonconductive adhesive layer 50, and the patient-contacting adhesive layer 90 are laminated on the main nonconductive support layer 146 in accordance with blocks 126-132, the bottom liner 78 may be disposed on the patient-contacting side 114 of the patient-contacting adhesive layer 90 (block 134). As noted above, the laminate assembly 44 produced in accordance with method 120 may be used, along with the emitter 36, the detector 28, and the sensor cable 16, to form the sensor body 40. Indeed, any or all of the blocks 122-134 of method 120 may be implemented as all or a portion of a manufacturing process to form a laminate assembly that may be used as a bandage sensor precursor.

Figure 6:
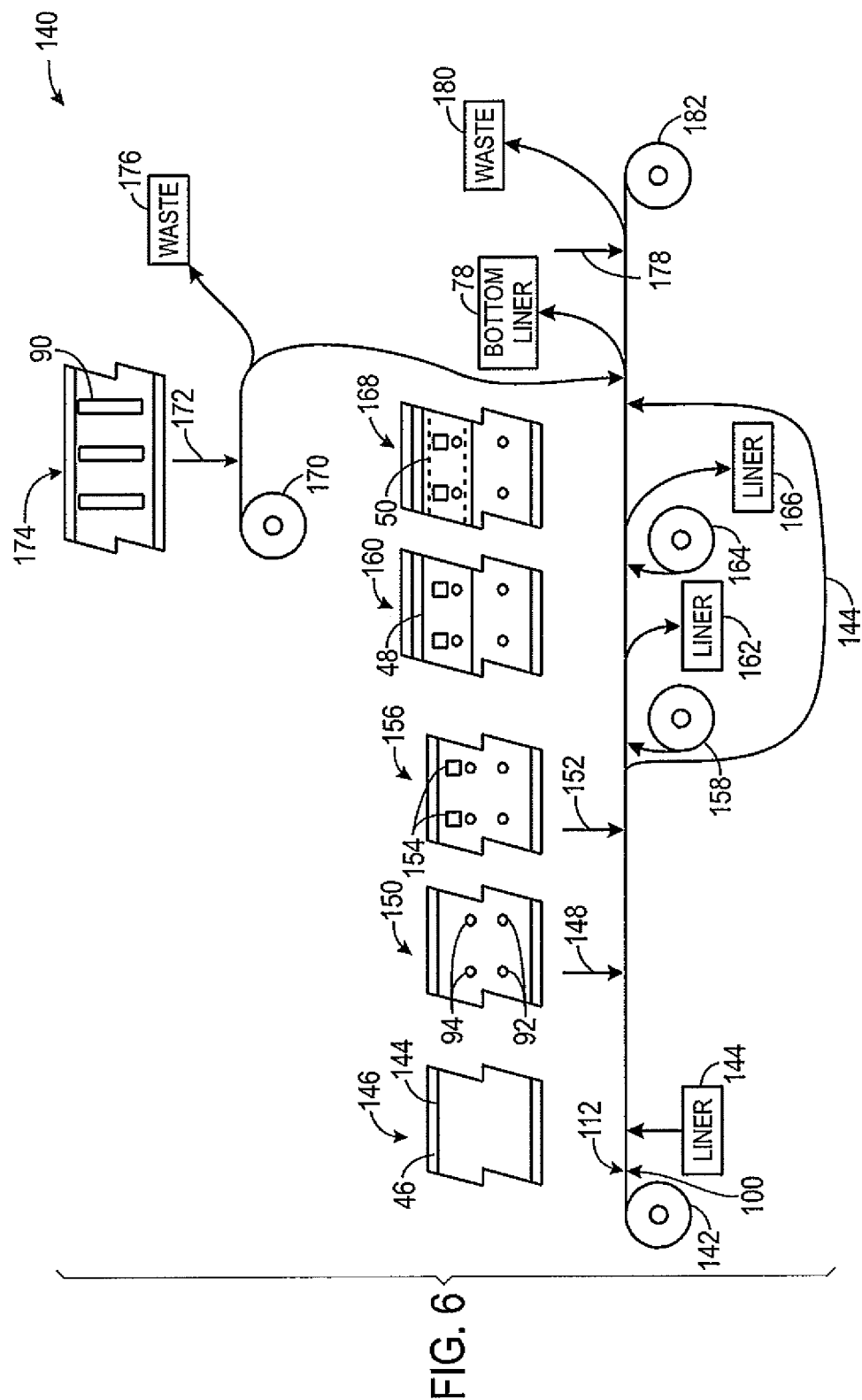
FIG. 6 is a process diagram illustrating an embodiment of a process for producing a roll of the laminate assembly used to produce a plurality of bandage sensors in accordance with an embodiment of the present disclosure.

FIG. 6 illustrates one such embodiment of a manufacturing process 140. The manufacturing process 140 includes providing a roll 142, which is unwound to expose the first and second surfaces 100, 112 of the of the main nonconductive support layer 46. The roll 142, as noted above with respect to the discussion of the main nonconductive support layer 46, may be a roll of polymeric material, such as polyethylene, polypropylene, polyvinylchloride, polyurethane, or a similar polymer. A top liner 144 is then laminated on the first side 100 of the main nonconductive support layer 46, which may protect the first side 100 from dust or other debris that may be encountered during the manufacturing process. As an example, a first cutout representation 146 depicts the arrangement of the top liner 144 disposed on the first side 100 of the main nonconductive support layer 46.

After the top liner 144 is laminated, the optical windows 92, 94 are formed in the main nonconductive support layer 46 by a die-cut procedure 148, illustrated as an arrow. As depicted by a second cutout representation 150, the first and second optical windows 92, 94 are formed across a width of the main nonconductive support layer 46. In other manufacturing process embodiments, the first and second optical windows 92, 94 may be formed along the length of the main nonconductive support layer 46. In such embodiments, the second cutout representation 150 would depict the first and second optical windows 92, 94 in a side-by-side arrangement, rather than a top-to-bottom arrangement as illustrated in the present embodiment. As will be discussed below, forming the first and second optical windows 92, 94 in the depicted orientation may facilitate the lamination of the ECATT layer 48 and the nonconductive adhesive layer 50 on the main nonconductive support layer 46.

After the optical windows are formed, a printing process 152 is performed, as depicted by an arrow. The printing process 152 may include printing an opaque ink 154 (e.g., a white ink) over a portion of the nonconductive support layer 46. As illustrated by the third cutout representation 156, the opaque ink 154 may be printed in patches or any similar pattern proximate the second optical windows 92. In certain embodiments, the opaque ink 154 may correct for wavelength shifts that may be caused by certain of the conductive fillers within the ECATT layer 48. Additionally, the opaque ink 154 may prevent reflection by the conductive fillers or other internal features of the bandage sensor 14. It should be noted that in embodiments where an optical window is formed in the ECATT layer 48, the printing process 152 may not be performed.

The top liner 144 may be removed after the printing process 152, which exposes the first side 100 of the main nonconductive support layer 46 for lamination. Accordingly, a roll 158 of the ECATT layer 48 (e.g., a roll of 3M™ 9713 XYZ-axis electrically conductive tape) may be provided and laminated along a portion of the roll 142 of the main nonconductive support layer 46. As noted above, in the orientation depicted, the second optical windows 94 are in a side-by-side arrangement. Keeping in mind that the second optical windows 94 are configured to receive the detector 28, the ECATT layer 48 may be laminated in a substantially continuous fashion down the length of the roll 142 over the second optical windows 94 without additional procedures, such as repetitive cutting, repetitive aligning, and so forth. The resulting arrangement is depicted in a fourth cutout representation 160, which illustrates the ECATT layer 48 as being laminated in a continuous fashion over the second optical windows 94. Additionally, as the ECATT layer 48 is laminated, a liner 162 may be removed from the roll 158 of the ECATT layer 48.

After the ECATT layer 48 is laminated on the main nonconductive support layer 46, a roll 164 of the nonconductive adhesive layer 50 (e.g., a roll of 3M™ 1516 single coated polyester medical tape) is provided, separated from a liner 166, and laminated over the ECATT layer 48 as it is unwound. The nonconductive adhesive layer 50 is depicted as a dashed line in a fifth cutout representation 168. Again, as noted above, the orientation of the second optical windows 94 enables the nonconductive adhesive layer 50 to be laminated in a substantially continuous fashion, rather than in a series of cuts, alignments, and laminations. After the nonconductive adhesive layer 50 is laminated, the top liner 144 is added back over or a new liner is put on the main nonconductive support layer 46, the ECATT layer 48, and the nonconductive adhesive layer 50.

Before, during, or after performing the laminations above, a roll 170 of the patient-contacting adhesive layer 90, which may be a double-sided adhesive layer, may be provided. The roll 170 may be double lined, or may be self-wound. As the roll 170 is unwound, a die-cutting procedure 172, illustrated as an arrow, may be performed. As illustrated in the sixth cutout representation 174, the die-cutting procedure 172 may produce a series of individual patient-contacting adhesive layers 90 on the roll 170. Adhesive portions of the roll 170 that do not form the patient-contacting adhesive layers 90 may be discarded as waste 176, recycled, or repurposed for further use. The patient-contacting adhesive layers 90 are then laminated over the second side 112 of the main nonconductive support layer 46, such that each patient-contacting adhesive layer 90 covers a pair of first and second optical windows 92, 94.

After the ECATT layer 48, the nonconductive adhesive layer 50, and the patient-contacting layer 90 have been laminated on the main nonconductive support layer 46, the bottom release liner 78 may be removed. Subsequently, a die-cutting 178 may be performed. For example, the die-cutting 178 may include shearing through all of the layers to form a plurality of laminate assemblies 44. The resulting die-cut material may be separated from waste 180, which may be discarded, recycled, or repurposed for future use. The resulting plurality of laminate assemblies 44, connected by the release liner 144, may be re-wound into a laminate assembly roll 182.

Figure 7:
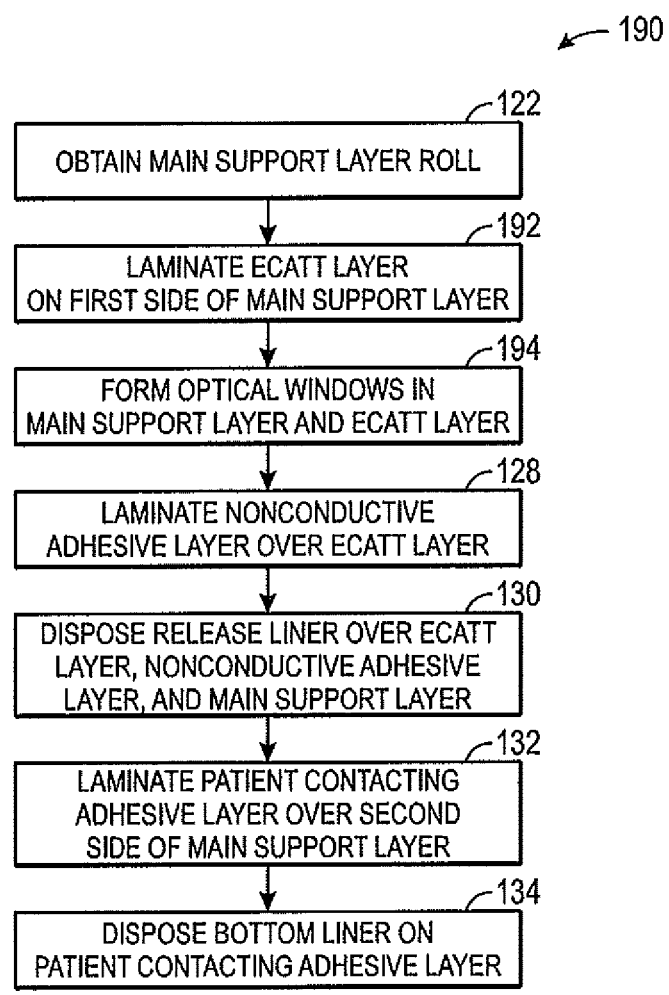
FIG. 7 is a process flow diagram illustrating an embodiment of a method for producing the sensor body of FIGS. 2 and 3, in accordance with an embodiment of the present disclosure.

While the method 120 and the manufacturing process 140 embodiments described above with respect to FIGS. 5 and 6, respectively, describe the construction of the laminate assembly 44 using a transparent ECATT layer, in other embodiments, it may be desirable to provide optical windows in the ECATT layer 48. For example, such optical windows may be desirable in embodiments where the ECATT layer 48 includes a tape that does not have a desirable amount of transparency with respect to the wavelengths of light monitored by the detector 28. Accordingly, an assembly method may be performed that includes forming one or more optical windows in the ECATT layer 48. FIG. 7 is a process flow diagram of one such method 190 for producing a laminate assembly 44 having an optical window in the ECATT layer 48. It should be noted that several of the acts of the method 190 may be performed in a similar or identical manner to the corresponding acts of the method 120 described with respect to FIG. 5.

The method 190 begins with obtaining the main nonconductive support layer 46, which may be performed as described above with respect to block 122 of FIG. 5. Prior to forming the optical windows in the main nonconductive support layer 46 as in method 120 and the process 140, the ECATT layer 48 is laminated on the first side 100 of the main nonconductive support layer 46 (block 192). For example, the ECATT layer 48 may be laminated on a portion of the main nonconductive support layer 46 corresponding to the placement of the detector 28.

After the ECATT layer 48 is laminated on the main nonconductive support layer 46, the first and second optical windows 92, 94 may be formed in the main nonconductive support layer 46, with at least one optical window being formed in the ECATT layer 48 (block 194). For example, the first and second optical windows 92, 94, as discussed above with respect to FIG. 6, may be formed by a die-cutting process.

After the optical windows 92, 94 have been formed, the remainder of the method 190 may be performed as described above with respect to FIG. 5. That is, the nonconductive adhesive layer 50 may be laminated on the ECATT layer 48 (block 128) followed by disposing a release liner over the ECATT layer 48, the nonconductive adhesive layer 50, and the main nonconductive support layer 46 (block 130). The patient-contacting adhesive layer 90 may then be laminated over the second side 112 of the main nonconductive support layer 46, followed by disposing the bottom release liner 78 on the patient-contacting side 114 of the patient-contacting adhesive layer 90 (block 134).

In addition to or in lieu of providing the ECATT layer 48 with or without an optical window, the ECATT layer 48 may be laminated on the main nonconductive support layer 46 in a variety of different arrangements. For example, as discussed in detail below with respect to FIGS. 8-21, the ECATT layer 48 may be a strip lined over a detector area of the main nonconductive support layer 46, or may also cover an additional portion of the main nonconductive support layer 46 to provide a cable termination area for the sensor cable 16 using features other than the drain wire 60.

Figure 8:
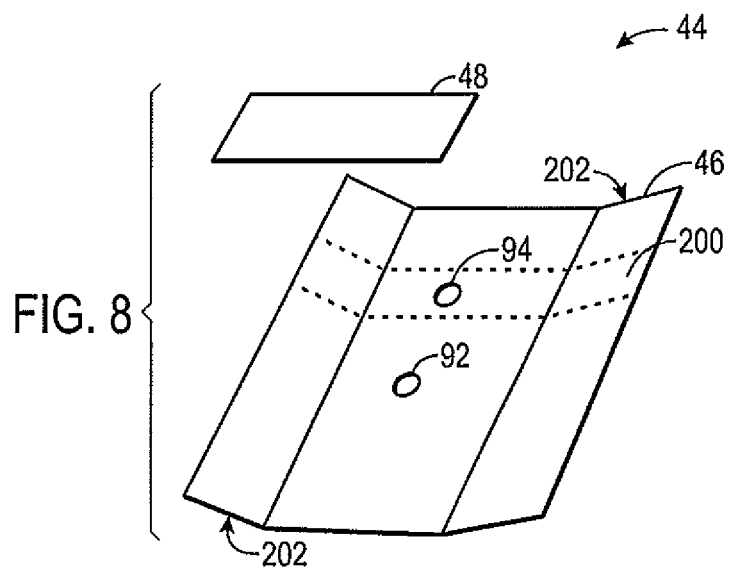
FIG. 8 is an exploded perspective view of an embodiment of an electrically conductive adhesive transfer tape layer and a main nonconductive support layer, in accordance with an embodiment of the present disclosure.

For example, FIG. 8 depicts an embodiment of a portion of the laminate assembly 44 where the ECATT layer 48 is a strip that is laminated over the second window 94 of the main nonconductive support layer 46. Alternatively or additionally, such as when no optical windows have been formed in the main nonconductive support layer 46, the ECATT layer 48 may be laminated over a detector area 200. The manner in which the main nonconductive support layer 46 may be folded so as to shield the detector 28 is illustrated by folds 202 in the main nonconductive support layer 46.

Figure 9:
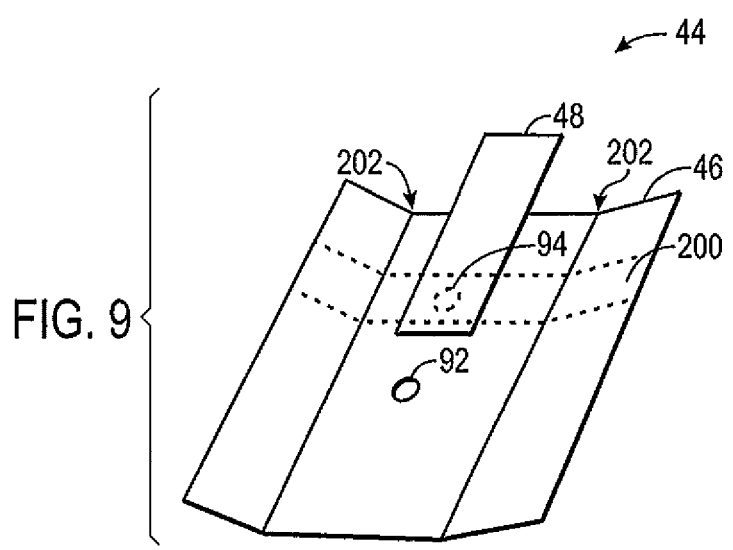
FIG. 9 is an exploded perspective view of an embodiment of an electrically conductive adhesive transfer tape layer and a main nonconductive support layer, in accordance with an embodiment of the present disclosure.

Similarly, FIG. 9 depicts the ECATT layer 48 as being oriented crosswise relative to the main nonconductive support layer 46. Thus, the ECATT layer 48 may be folded vertically over the detector 28, as depicted in the embodiment of FIG. 9, or may be folded horizontally over the detector 28, as depicted in FIG. 8. In embodiments where the ECATT layer 48 is folded vertically over the detector 28, the detector 28 may be insulated before the main nonconductive support layer 46 is folded at folds 202, as discussed below with respect to FIG. 21.

Figure 10:
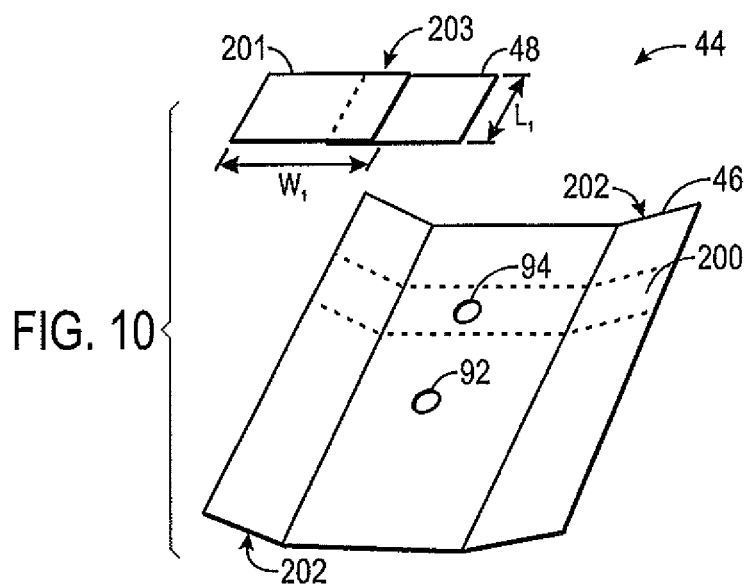
FIG. 10 is an exploded perspective view of an embodiment of a first electrically conductive adhesive transfer tape layer coupled to a second electrically conductive adhesive transfer tape layer and a main nonconductive support layer, in accordance with an embodiment of the present disclosure.

While FIGS. 8 and 9 illustrate embodiments in which a single ECATT layer 48 is used to shield the detector 28, in other embodiments, it may be desirable to use more than one ECATT layer, as depicted in FIG. 10. Specifically, FIG. 10 depicts an embodiment in which the ECATT layer 48 is positioned so as to cover the active face 98 of the detector 28, and is coupled to an additional ECATT layer 201, which is positioned so as to cover an opposite side of the detector 28. For example, in one embodiment, the ECATT layer 48 may be substantially transparent with respect to the wavelengths of light used for performing the pulse oximetry measurements, and the additional ECATT layer 201 may be substantially opaque with respect to the wavelengths of light. In other words, only the active face 98 of the detector 28 may be shielded with a transparent ECATT, while the remaining portions of the detector 28 are shielded with a non-transparent ECATT. In some embodiments, it may be desirable to ensure that the ECATT layers 48 and 201 are electrically connected so as to form a continuous Faraday shield around the detector 28. Thus, there may be an overlap 203 between the transparent ECATT layer 48 and the non-transparent additional ECATT layer 201. As an example embodiment, ECATT layer 48 may include 3M™ 9713 electrically conductive tape, the additional ECATT layer 201 may include 3M™ 9712 electrically conductive tape, and the overlap 203 may be approximately 0.05 inches for ECATT layers 48, 201 having a 0.5 inch width $w_1$ by a 0.60 inch length $l_1$, with the overlap 203 being across the width $w_1$ as illustrated (i.e., the ECATT layers 48, 201 are side-by side), or across the length $l_1$ in embodiments where the ECATT layers 48, 201 are vertically folded over the detector 28 (i.e., the ECATT layer 48 is below the additional ECATT layer 201). This overlapping configuration may be desirable in situations where the cost of the transparent ECATT layer 48 is greater than the cost of the non-transparent additional ECATT layer 201. Thus, the embodiment of FIG. 10 may aid in reducing the costs associated with shielding the detector 28.

Figure 11:
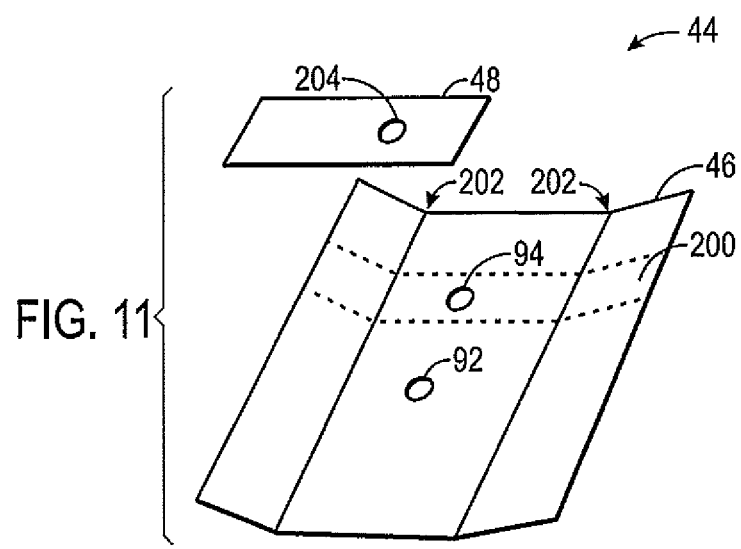
FIG. 11 is an exploded perspective view of an embodiment of an electrically conductive adhesive transfer tape layer and a main nonconductive support layer, the electrically conductive adhesive transfer tape layer having an optical window, in accordance with an embodiment of the present disclosure.

Alternatively or additionally, the active face 98 of the detector 28 may be partially or completely uncovered. FIG. 11 depicts the ECATT layer 48 as including an optical window 204 for the detector 28. The optical window 204 may be desirable in embodiments where the ECATT layer 48 does not have a desirable amount of transparency with respect to the monitored wavelengths of light. For example, the ECATT layer 48 of FIG. 11 may include 3M™ 9712 electrically conductive tape.

Figure 12:
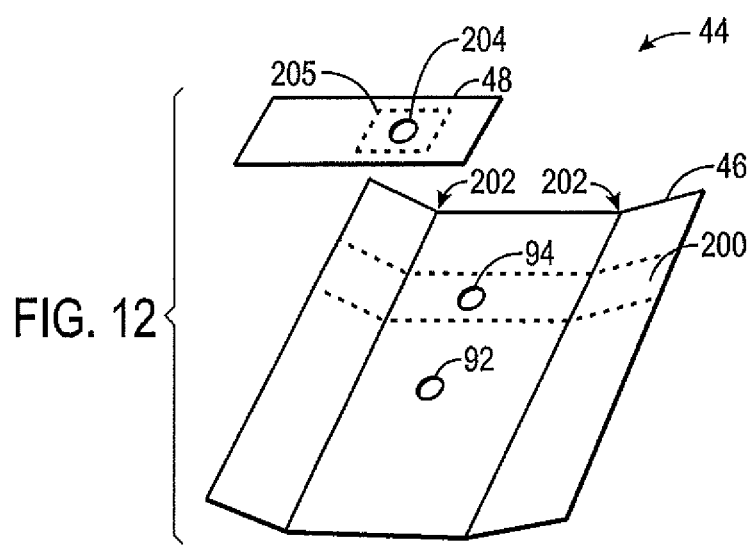
FIG. 12 is an exploded perspective view of an embodiment of an electrically conductive adhesive transfer tape layer and a main nonconductive support layer, the electrically conductive adhesive transfer tape layer having an optical window covered by an additional electrically conductive adhesive transfer tape layer, in accordance with an embodiment of the present disclosure.

While the embodiment of the laminate assembly 44 depicted in FIG. 11 may eliminate the use of a more costly ECATT layer 48 by providing the optical window 204, the ECATT layer 48 may not form a continuous structure. Because Faraday shields may have increased efficacy when the shielded material (i.e., the detector 28) is completely surrounded, it may be desirable to provide approximately 360° of coverage for the detector 28, rather than leaving the active face 98 of the detector 28 unshielded. Accordingly, FIG. 12 depicts an embodiment in which the optical window 204 of the ECATT layer 48 is covered or filled with an additional ECATT layer 205, which may be transparent with respect to the wavelengths of interest received by the detector 28. Indeed, the ECATT layer 48 and the additional ECATT layer 205 may overlap and be in continuous electrical contact such that approximately 360° of shielding is provided for the detector 28. As an example, the ECATT layer 48 may include 3M™ 9712 electrically conductive tape while the additional ECATT layer 205 may include 3M™ 9713 electrically conductive tape.

Figure 13:
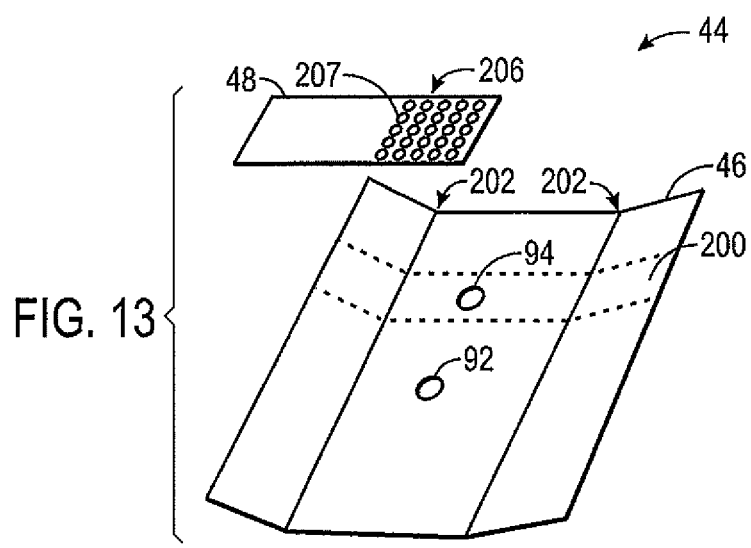
FIG. 13 is an exploded perspective view of an embodiment of an electrically conductive adhesive transfer tape layer and a main nonconductive support layer, the electrically conductive adhesive transfer tape layer having an optical grid, in accordance with an embodiment of the present disclosure.

As an alternative to using multiple ECATT materials, or in addition to using multiple ECATT materials, it may be desirable to enable desired wavelengths of light to pass through the ECATT layer 48 without the use of a large optical window 204 as in FIG. 11, even in embodiments where the ECATT layer 48 is non-transparent with respect to the desired wavelengths. In accordance with certain embodiments of the present disclosure, optical grids 206 may be formed in the ECATT layer 48, as depicted in FIGS. 13-15. In a general sense, the optical grids 206 disclosed herein may have any size, shape, or arrangement; though it may be desirable for the size of the optical grid 206 to generally correspond to the size of the active face 98 of the detector 28 so as to allow maximal light penetration while providing sufficient shielding coverage. In certain embodiments, the optical grids 206 may have a size that equals or exceeds the size of the second optical window 94. The optical grids 206 may be formed in the ECATT layer 48 using any suitable technique, such as die cutting, laser etching, chemical etching, or another lithographic technique.

In FIG. 13, the optical grid 206 includes a plurality of circular openings 207 formed in the ECATT layer 48. In one embodiment, the centers of the circular openings 207 may be spaced approximately 0.050 inches from one another. The circular openings 207, as depicted, are arranged in a regular, continuous pattern of rows and columns. However, as illustrated in FIG. 14, the optical grid 206 may include a plurality of circular openings 208 that are staggered. That is, the circular openings 208 are formed in alternating rows where every other row is aligned. As in FIG. 13, the circular openings 208 may be spaced approximately 0.050 inches from one another within each row, with each row being staggered by approximately 0.025 inches from an adjacent row.

In FIG. 15, the optical grid 206 includes a plurality of slits 209 that form regular rows and columns. However, as noted above with respect to the optical grid 206, the slits 209 may have any arrangement, such as a staggered pattern, a circular pattern, another pattern, or may be random. As an example, in one embodiment, the rows of the slits 209 may be separated by approximately 0.02 inches, each slit 209 may be approximately 0.02 inches, and the slits 209 may be separated by approximately 0.07 inches within each row.

In addition to providing shielding for the detector 28, the ECATT layer 48 may be laminated proximate (but not over) the first optical window 92 (i.e., the emitter window) to provide a termination area for termination wires of the sensor cable 16. An embodiment of such an arrangement is illustrated in FIG. 16. In the illustrated embodiment, the ECATT layer 48 is depicted as including three main sections: a detector-shielding section 210, a cable termination section 212, and a grounding section 214 that provides an electrical connection between the detector-shielding section 210 and the cable termination section 212. When the ECATT layer 48 is laminated on the main nonconductive support layer 46, the detector-shielding section 210 may be positioned over the detector area 200, as discussed above with respect to FIG. 8. The cable termination section 212 may be positioned over a cable entry area 216. For example, the cable entry area 216 may correspond to an area at which the sensor cable 16 enters the sensor body 40 and where the jacket 54 (FIG. 2) of the sensor cable 16 ceases to cover the plurality of wires 52 (FIG. 2). The grounding section 214 may be adapted and positioned so as to avoid electrical contact with the emitter 26 when the sensor body 40 is assembled, while grounding the detector-shielding section 210 to dissipate the blocked electromagnetic radiation.

It may be appreciated that the material used to form the ECATT layer 48 illustrated in FIG. 16 may be transparent to the optical wavelengths used in the measurements performed by the optical sensor. An embodiment where the material of the ECATT layer 48 is not transparent to these wavelengths is illustrated in FIG. 17. Accordingly, in the embodiment illustrated in FIG. 17, the ECATT layer 48 is depicted as having an optical window 218 to enable light to be received by the detector 28.

The arrangements illustrated in FIGS. 8-11 may each generally correspond to an embodiment of the acts represented by block 126 in FIG. 5 and/or block 192 of FIG. 7.

Figure 18:
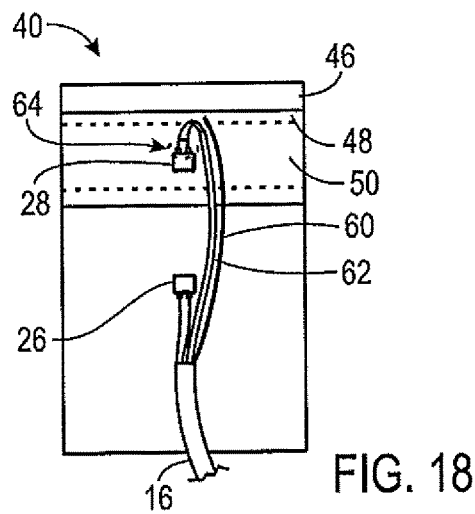
FIG. 18 is a top sectional view of an embodiment of a sensor body having a single strip of electrically conductive adhesive transfer tape for use as a Faraday shield for the detector, the transfer tape also serving to terminate a sensor cable of the sensor at an area proximate the detector, in accordance with an aspect of the present disclosure.

Indeed, such embodiments of block 126 and/or block 192 may be used to produce a variety of different arrangements of the sensor body 40, examples of which are illustrated diagrammatically in their unfolded configuration with respect to FIGS. 12-14. Specifically, FIG. 18 illustrates an embodiment where the ECATT layer 48 is lined as a substantially symmetrical strip over the main nonconductive support layer 46. As illustrated, the ECATT layer 48 in FIG. 18 is sized so as to cover the detector 28, the connection area 64, and at least a portion of the drain wire 60. In this embodiment, the drain wire 60 terminates in an area proximate the detector 28 (e.g., the detector area 200). Again, the nonconductive adhesive layer 50, as discussed above, insulates the detector 28 and the connection area 64 from the conductivity of the ECATT layer 48 while allowing a direct electrical connection between the drain wire 60 and the ECATT layer 48.

Figure 19:
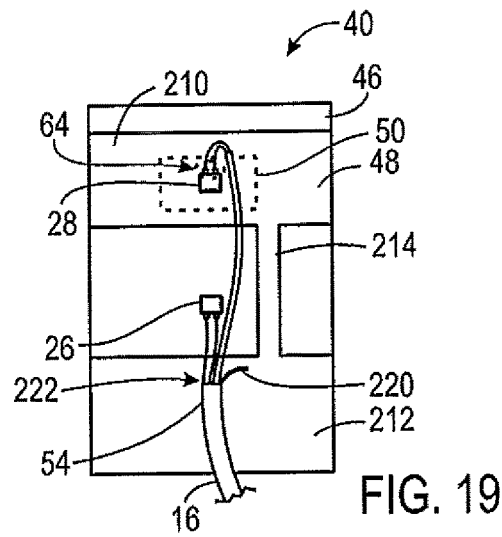
FIG. 19 is a top sectional view of an embodiment of a sensor body having a piece of sectioned electrically conductive adhesive transfer tape for use as a Faraday shield for the detector, the transfer tape also serving to terminate a sensor cable of the sensor by connecting to a drain wire at an area proximate the emitter, in accordance with an aspect of the present disclosure.

In FIG. 19, the sensor body 40 is formed by laminating the ECATT layer 48 on the main nonconductive support layer 46 as depicted in FIGS. 10 and 11. As noted above with respect to the discussion of these figures, the ECATT layer 48 includes the detector-shielding section 210, the cable termination section 212, and the grounding section 214. As will be appreciated with reference to the illustrated embodiment, such a configuration of the ECATT layer 48 may be desirable in arrangements where the sensor cable 16 includes a relatively short drain wire 220. Accordingly, the cable termination section 212 may be sized so as to cover the entry of the sensor cable 16 into the sensor body 40, an area 222 where the cable jacket 54 ceases to cover the plurality of wires 52, and the termination of the short drain wire 220.

Figure 20:
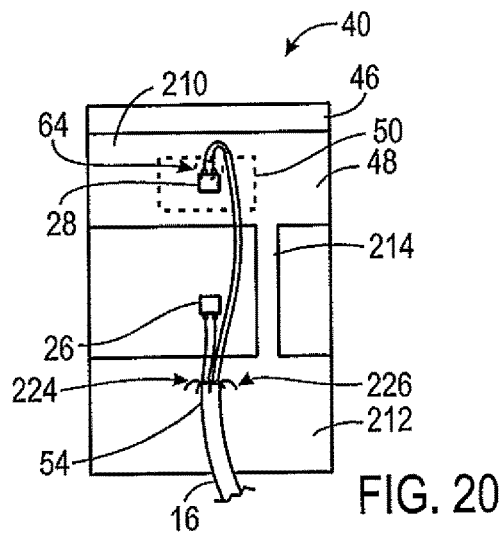
FIG. 20 is a top sectional view of an embodiment of a sensor body having a piece of sectioned electrically conductive adhesive transfer tape for use as a Faraday shield for the detector, the transfer tape also serving to terminate a sensor cable of the sensor by connecting to a plurality of cable termination wires at an area proximate the emitter, in accordance with an aspect of the present disclosure.

In a similar manner to the configuration of FIG. 19, the embodiment illustrated in FIG. 20 depicts the ECATT layer 48 as having the detector-shielding section 210, the cable termination section 212, and the grounding section 214. However, the sensor cable 16 is illustrated as terminated by a plurality of termination wires 224 that are folded back over the cable jacket 54. Such a termination technique may provide enhanced termination for the sensor cable 16 compared to a single drain wire. Accordingly, the cable termination section 212 of the ECATT layer 48 is sized so as to cover at least the entry of the sensor cable 16 into the sensor body 40 and a termination area 226 where the plurality of termination wires 224 extend over the cable jacket 54. The nonconductive adhesive layer 50 may cover only a small portion of the detector-shielding section 210, or may run as a strip across the detector-shielding section 210 as depicted in FIG. 18.

Figure 21:
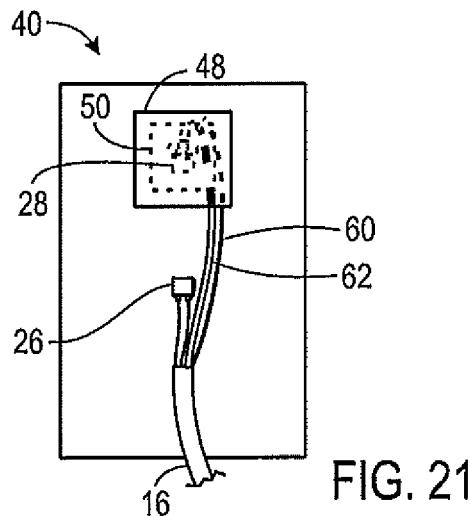
FIG. 21 is a top sectional view of an embodiment of an unfolded sensor body having an electrically conductive adhesive transfer tape folded about the detector to shield the detector, the transfer tape also serving to terminate a sensor cable of the sensor by connecting to a plurality of cable termination wires at an area proximate the detector, in accordance with an aspect of the present disclosure.

Indeed, various configurations of the ECATT layer 48 and the nonconductive adhesive layer 50 may be implemented depending upon the placement of the detector 28, the emitter 26, cable termination wires, or other sensor features. Accordingly, other shapes, sizes, and arrangements of the ECATT layer 48 and the nonconductive adhesive layer 50 are considered to be within the scope of the present disclosure. For example, while the embodiments depicted in FIGS. 18-20 depict the ECATT layer 48 as unfolded as the emitter 26, detector 28, and other electronic components are placed on the main nonconductive support layer 46, it should be noted that the ECATT layer 48 and nonconductive adhesive layer 50 may be disposed (e.g., folded) over the detector 28 before placement onto the main nonconductive support layer 46. Accordingly, FIG. 21 depicts an embodiment where the ECATT layer 48 is folded over the nonconductive adhesive layer 50, the detector 28, the connection area 48, and a portion of the drain wire 60 before placement onto the main nonconductive support layer 46.

Figure 22:
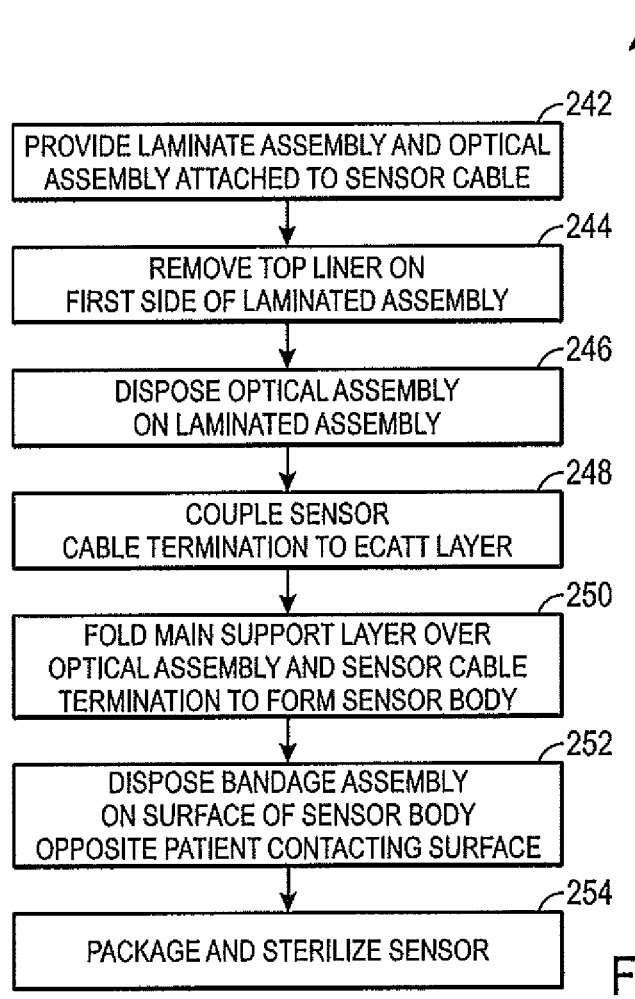
FIG. 22 is a process flow diagram illustrating an embodiment of a method for producing a bandage sensor having an electrically conductive adhesive transfer tape, in accordance with an aspect of the present disclosure.

Keeping in mind the foregoing descriptions of the manner in which the various portions of the bandage sensor 14 are assembled, the present embodiments provide a method 240, illustrated in FIG. 22, for producing a medical sensor (e.g., the bandage sensor 14), having an ECATT layer as a Faraday shield. The method 240 begins with providing the laminate assembly 44, an optical assembly (e.g., the emitter 26, the detector 28, and other optical features), and the sensor cable 16 (block 242). The top liner 144 is then removed from the laminate assembly 44 (block 244). The emitter 26 and the detector 28 are then positioned on the laminate assembly 44 (block 246). As discussed above, the detector 28 may be placed in direct contact with the nonconductive adhesive layer 50 such that the detector 28 is shielded from EMI/RFI by the ECATT layer 48 but is electrically insulated from the same.

Substantially concurrently to performing the acts represented by block 246, the termination features of the sensor cable 16 may be connected to the ECATT layer 48 (block 248). As noted above, the termination features of the sensor cable 16 may be coupled to the ECATT layer 48 via the adhesive surfaces of the ECATT layer 48, rather than via a soldering procedure as is performed for fully metallic Faraday shields. As an example, the termination features of the sensor cable 16 may be attached to the ECATT layer 48 in a manner consistent with the illustrations of FIGS. 18-20. After the optical assembly, the sensor cable 16, and the cable termination features have been suitably positioned on the laminate assembly 44, the main support layer 46 may be folded over the optical assembly and the sensor cable (and termination features) to form the sensor body 40 (block 250). For example, as depicted by the folds in the main nonconductive support layer 46 in FIGS. 4 and 8-17, one portion of the laminate assembly 44 is folded over the emitter 26, the detector 28, and the sensor cable 16, followed by a remaining portion.

Once the sensor body 40 is formed, a bandage layer or a plurality of bandage layers (e.g., the bandage top assembly 70 of FIG. 3) is laminated on the sensor body 40 (block 252). For example, as depicted in FIG. 3, the metallic layer 72 of the bandage top assembly 70 may be laminated over the non-patient contacting surface 74 of the sensor body 40. The bandage layer 24 may be laminated onto the surface 76 of the bottom release liner 78. Thereafter, the sensor cable 16 may be wrapped, the sensor bandage 14 may be placed into a package, and the package may be sterilized, pasteurized, or otherwise cleaned in any suitable manner (block 254). The sterilized bandage sensor 14 then may be sent to a medical facility.

Figure 23:
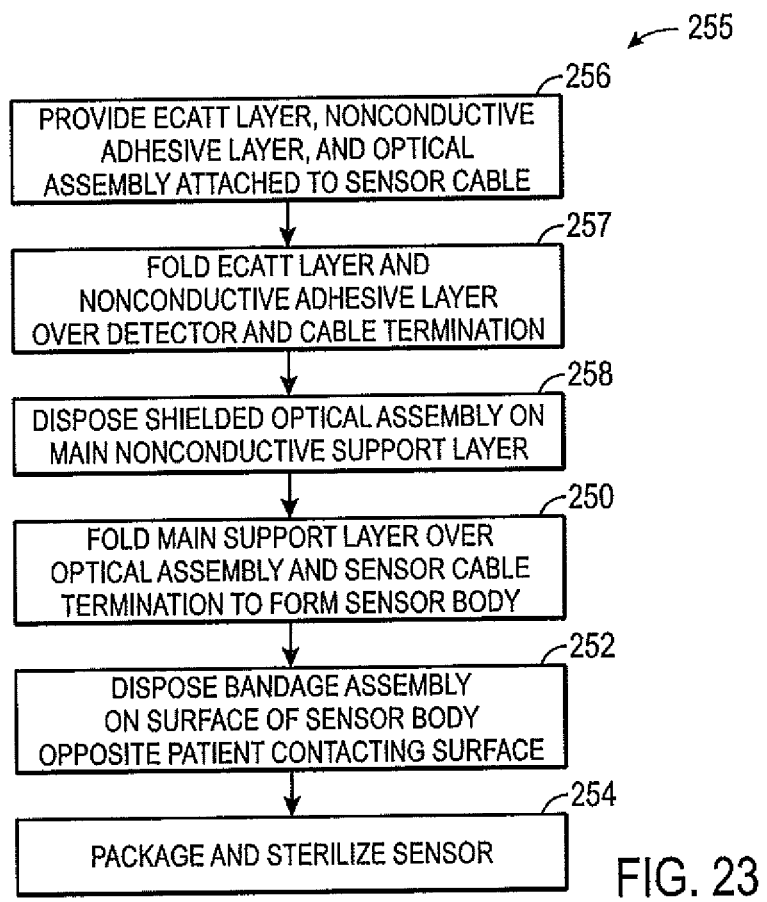
FIG. 23 is a process flow diagram illustrating an embodiment of a method for producing a bandage sensor having an electrically conductive adhesive transfer tape, in accordance with an aspect of the present disclosure.

As noted with respect to FIG. 21, the detector 28 may be provided in combination with the ECATT layer 48 and the nonconductive adhesive layer 50 before the sensor body 40 is formed. Accordingly, FIG. 23 depicts an embodiment of a method 255 for producing the bandage sensor 14 by providing a pre-insulated detector 28. The method 255 includes providing the ECATT layer 48, the nonconductive adhesive layer 50, and the optical assembly (i.e., the emitter 26 and detector 28) connected to the sensor cable 16 (block 256). The ECATT layer 48 and the nonconductive adhesive layer 50 may then be folded over the detector 28 (block 257) such that the detector 28 is electrically insulated from the ECATT layer 48 but is shielded from EMI/RFI.

The shielded optical assembly may then be disposed on the main nonconductive support layer 46 (block 258), for example as depicted in FIG. 21. In a similar manner to the acts described above with respect to FIG. 22, the main nonconductive support layer 46 may be folded over the optical assembly and the sensor cable 16 to form the sensor body 40 (block 250). The bandage top assembly 70 may be disposed on the sensor body 40 (block 252) as described above. The bandage sensor 14 produced from the acts described above may then be packaged. The packaged product can either be sterilized (block 254) and shipped to a medical facility or sent directly to the medical facility without sterilization.

In addition to or in lieu of producing a medical sensor having a flexible, electrically conductive transfer tape layer as a Faraday shield using the approaches described above, it may be desirable to enhance the flexibility and EMI/RFI shielding of the sensor cable 16. Accordingly, the present embodiments also provide approaches that may result in increased flexibility, and enhanced EMI/RFI shielding (i.e., reduced noise in the signals of interest) of the sensor cable 16. Indeed, while the present approaches toward increasing the flexibility of such a cable are presented in the context of the sensor cable 16, it should be noted that the approaches described herein are also applicable to many types of cables, such as cables commonly used in the medical industry (e.g., adapter cables, extension cables, patient interface cables), and the like.

In accordance with certain aspects of the present embodiments, the flexibility and shielding ability of the sensor cable 16 may be enhanced using a conductive polymer. In some embodiments, the conductive polymer may include a conductive filler disposed within a polymer matrix. The conductive polymer may be used to provide EMI/RFI shielding for the jacketed wires (e.g., wires 56, 58, FIG. 2) that run through the sensor cable 16. In some embodiments, the polymer portion of the conductive polymer may include any flexible polymeric material such as polyvinylchloride (PVC), polyolefins (e.g., polyethylene, polypropylene), polyamides (e.g., nylon-6), synthetic or natural elastomers (e.g., neoprene), various other thermoplastics (e.g., thermoplastic chlorinated polyethylene (CPE)), or any combination thereof. In certain embodiments, at least a portion of the conductive polymer may be a polymer having at least some degree of electrical conductivity such that the polymer is not an electrically insulative material. That is, the polymer may be an intrinsically conductive polymer. Examples of such polymers include polyacetylene, polythiophene, poly(p-phenylenevinylene), polyphenylene sulfide, polyaniline, and other fully-conjugated polyhydrocarbyl materials, such as polyaromatics, polyheteroaromatics, and so on.

The conductive filler may include, in some embodiments, any micro- or nano-scale material (i.e., a material having at least one dimension on the micro- or nano-scale) that is capable of conducting electricity. As an example, the conductive filler may include micro or nanofibers made from conductive or semiconductive materials (e.g., stainless steel fibers, carbon nanotubes, silicon nanotubes, silver fibers, copper fibers), conductive particulates (e.g., nickel powder, gold powder, copper powder, gold-plated nickel fillers), or any combination thereof. Indeed, any conductive filler capable of rendering a mixture of the polymer and conductive filler suitable for shielding wires from EMI/RFI, while maintaining certain desirable properties of the polymer (e.g., strength, flexibility), are within the scope of the present disclosure.

Indeed, the conductive filler may be added to the polymer matrix in an amount such that the polymer and conductive filler may together form a continuous EMI/RFI shield for the wires within the sensor cable 16. In certain embodiments, the conductive polymer may retain the flexibility of the polymer (i.e., the substantially pure polymer), or a desired percentage of the flexibility of the polymer. For example, in certain embodiments, the conductive polymer may retain between approximately 20 and 100 percent (e.g., between approximately 30 and 100%, 40 and 90%, or 50 and 80%) of the flexibility of the pure polymer. It will be appreciated that the amount of conductive filler added to the polymer matrix may therefore depend at least on the conductivity of the filler and the effect that the filler has on the overall flexibility of the mixture.

Figure 26:
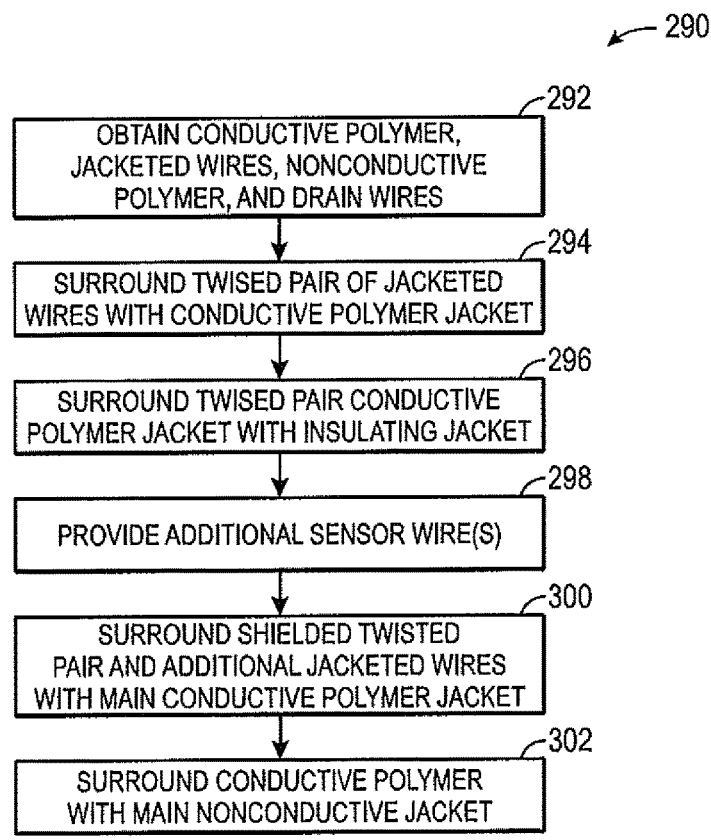
FIG. 26 is a process flow diagram illustrating an embodiment of a method for producing the sensor cable of either of FIG. 16 or 17, in accordance with an aspect of the present disclosure.
Figure 27:
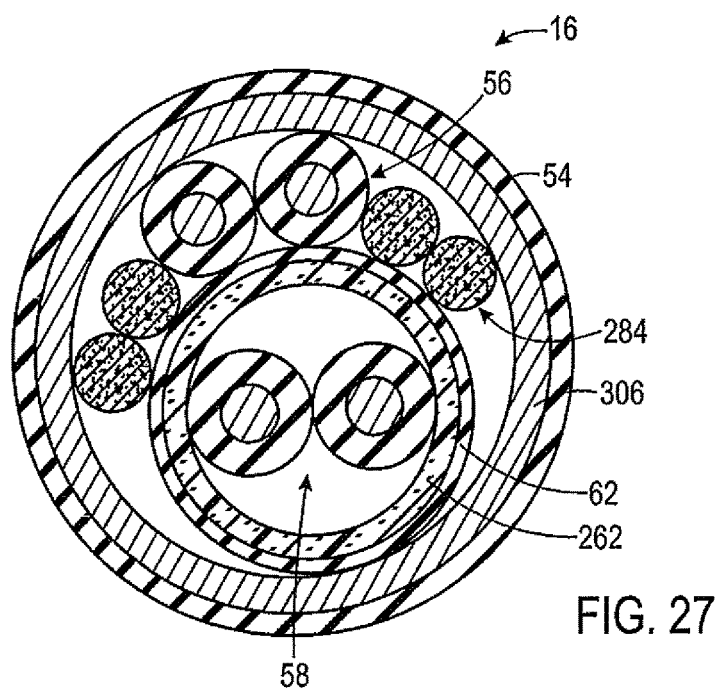
FIG. 27 is a cross-sectional view of the sensor cable taken along line 16-16 of FIG. 2 and illustrating a main fully metallic EMI/RFI shielding jacket and a secondary conductive polymer EMI/RFI shielding jacket, in accordance with an aspect of the present disclosure.
Figure 28:
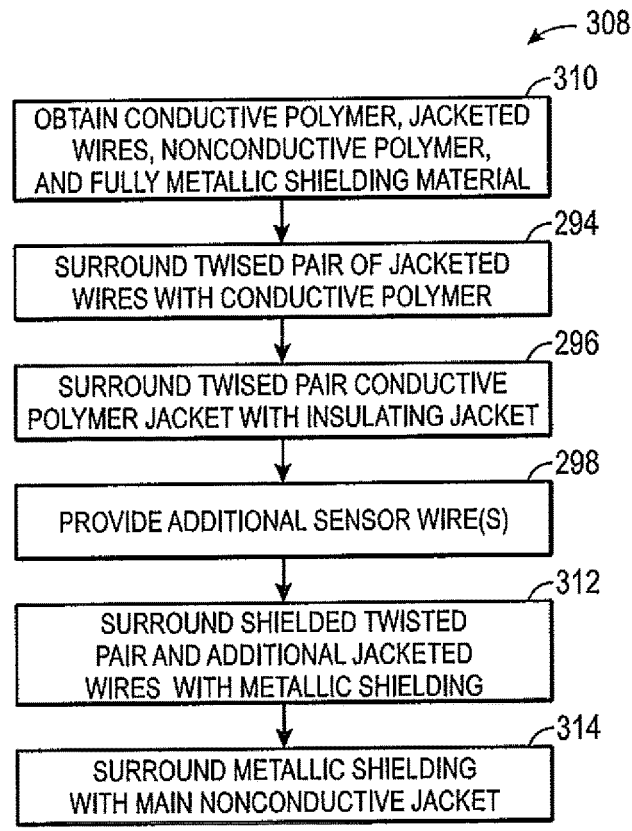
FIG. 28 is a process flow diagram illustrating an embodiment of a method for producing the sensor cable of FIG. 27, in accordance with an aspect of the present disclosure.
Figure 29:
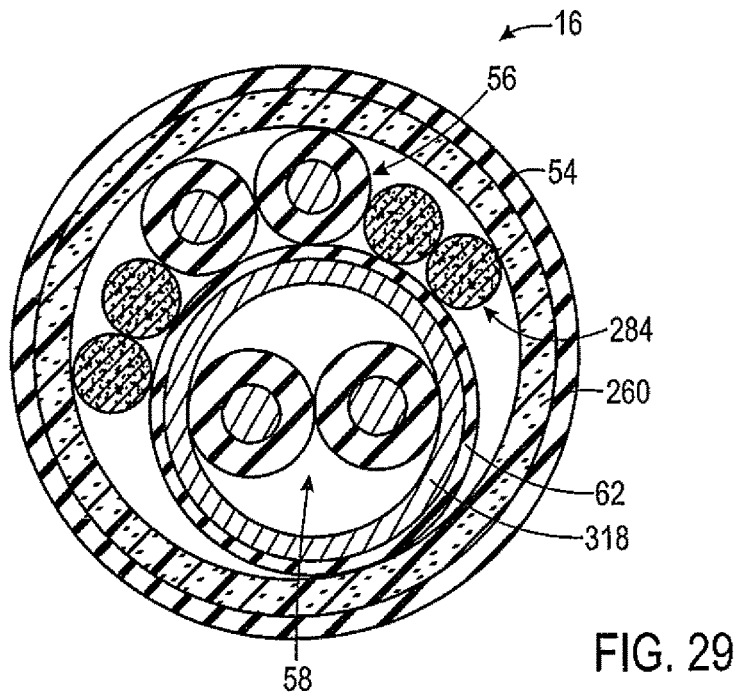
FIG. 29 is a cross-sectional view of the sensor cable taken along line 16-16 of FIG. 2 and illustrating a main conductive polymer EMI/RFI shielding jacket and a secondary fully metallic EMI/RFI shielding jacket, in accordance with an aspect of the present disclosure.

In addition to providing enhanced flexibility, the conductive polymer may also provide enhanced durability and reliability compared to other cable shielding techniques. Indeed, the conductive polymer may be used in lieu of, or in addition to, other EMI/RFI shielding features such as wire strands. For example, some shielding features may include a plurality of metallic strands that are twisted or braided and surround the jacketed wires (e.g., wires 56, 58, FIG. 2) that carry the signals of interest (e.g., pulse oximetry signals, electrocardiogram signals). In one embodiment, the conductive polymers in accordance with the present disclosure may be used in lieu of these twisted wire strands, providing enhanced flexibility and EMI/RFI shielding. For example, as the wire strands used for shielding are exposed to repeated bending, twisting, and other forces during the course of normal use, the strands may begin to separate from one another and/or deform and lose conductivity. This separation and/or loss in conductivity may be undesirable, as the wavelength(s) of the blocked electromagnetic radiation that is shielded by the wire strands may be smaller than the areas between the wire strands and/or or the conducting portions of the wire strands. This may allow the electromagnetic radiation to interfere with the signals of interest carried by the jacketed wires. Moreover, this degradation in shielding ability may also lead to crosstalk between jacketed wires. The use of the conductive polymers in accordance with the present disclosure overcomes these and other shortcomings of such wire strands by providing a continuous, flexible shielding material for the jacketed wires. Indeed, the materials used to construct the conductive polymers may be selected based on their flexibility, conductivity, and/or other attributes, as noted above. Embodiments of such approaches are discussed with respect to FIGS. 24-30. Specifically, in FIGS. 24-29, embodiments of the sensor cable 16 are presented wherein conductive polymers in accordance with the present disclosure are used for shielding the wires 56, 58 from EMI/RFI. In FIGS. 27-29, embodiments of the sensor cable 16 are presented wherein the conductive polymers are used in addition to fully metallic shielding features.

Figure 24:
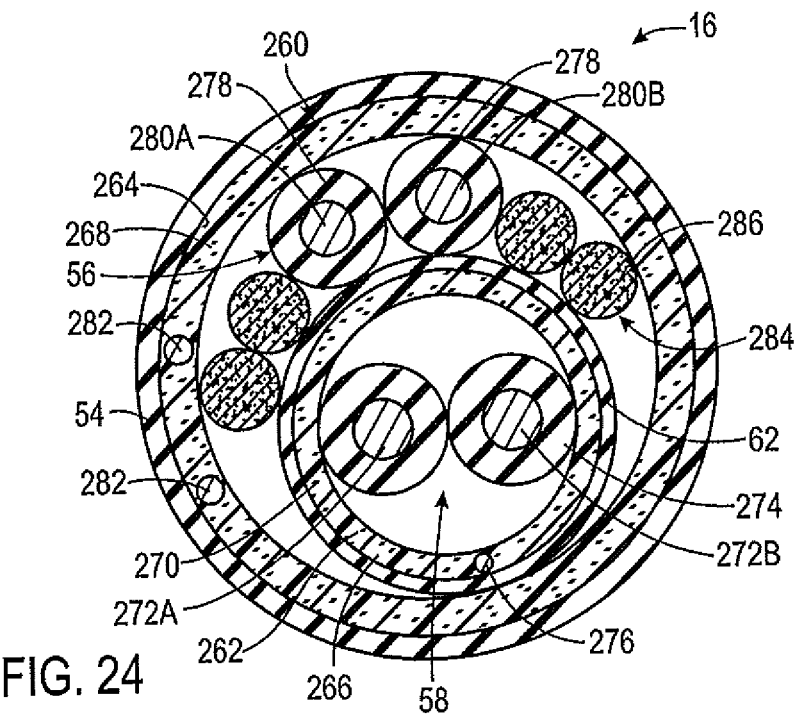
FIG. 24 is a cross-sectional view of the sensor cable taken along line 16-16 of FIG. 2 and illustrating a main conductive polymer EMI/RFI shielding jacket and a secondary conductive polymer EMI/RFI shielding jacket, in accordance with an aspect of the present disclosure.

Moving to FIG. 24, an embodiment of the sensor cable 16 is depicted having a main conductive polymer jacket 260 and a second conductive polymer jacket 262 surrounding the second pair of wires 58. The main conductive polymer jacket 260 and the second conductive polymer jacket 262 each include respective first and second polymeric matrices 264, 266 and respective first and second conductive fillers 268, 270 disposed within their respective polymeric matrices 264, 266. The first and second polymeric matrices 264, 266 may be the same, or may be different, and may independently include any or a combination of the polymer materials listed above. Similarly, the first and second conductive fillers 268, 270 may be the same or different, and each may independently include any or a combination of the conductive filler materials mentioned above.

Figure 25:
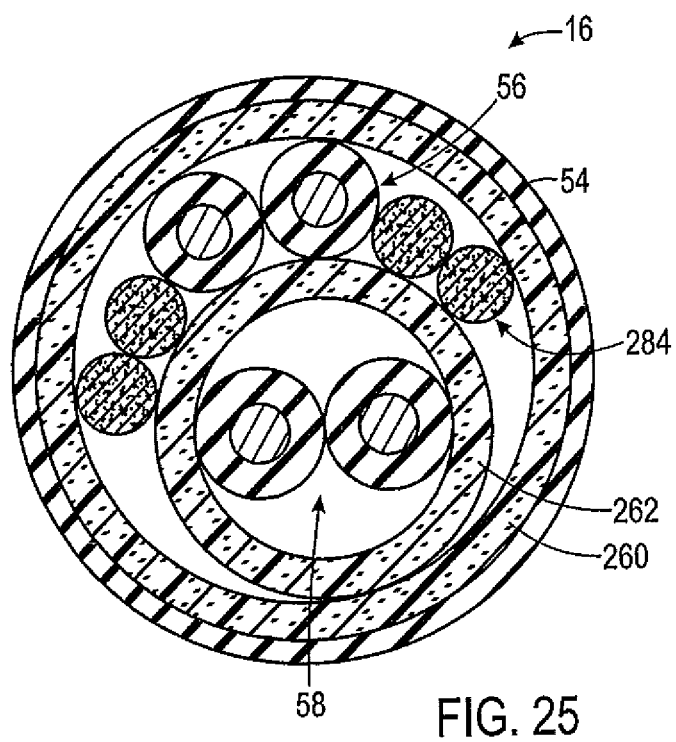
FIG. 25 is a cross-sectional view of the sensor cable taken along line 16-16 of FIG. 2 and illustrating a main conductive polymer EMI/RFI shielding jacket and a secondary conductive polymer EMI/RFI shielding jacket, the main and the secondary jackets being in contact with one another, in accordance with an aspect of the present disclosure.

The second conductive polymer jacket 262 may provide EMI/RFI shielding for the second pair of wires 58. Generally, the second pair of wires 58, as discussed above with respect to FIG. 2, may each include a conductor 272 (e.g., a conductive wire) and a nonconductive insulating jacket 274 surrounding each conductor 272. The second pair of wires 58 may be adapted to provide power to and carry signals of interest from the detector 28. In some embodiments, the second conductive polymer jacket 262 may also include a drain wire 276 to enable termination of the second conductive polymer jacket 262 at the sensor (e.g., the bandage sensor 14 of FIG. 2) and/or the cable connector (e.g., the sensor cable connector 18 of FIG. 1). However, in some embodiments, such as when the sensor cable 16 is attached to a bandage sensor 14 having an electrically conductive transfer tape Faraday shield, the sensor cable 16 may be terminated without the use of a drain wire. Such an embodiment is illustrated in FIG. 25. For example, the second conductive polymeric jacket 262 may attach directly to the transfer tape Faraday shield (e.g., the ECATT layer 48 of FIG. 2) via the adhesive of the transfer tape.

Returning to FIG. 24, in addition to providing EMI/RFI shielding for the second pair of wires 58, the second conductive polymeric jacket 262 may prevent cross-talk between the second pair of wires 58 and the first pair of wires 56. As noted above, the first pair of wires 56 are adapted to be in operative connection with the emitter 26. Accordingly, the second conductive polymeric jacket 262 may be electrically separated from the first pair of wires 56 at least by nonconductive jacketing 278 surrounding each conductor 280 of the first pair of wires 56. In the illustrated embodiment, the second conductive polymeric jacket 262 is also electrically separated from the first pair of wires 56 by the nonconductive jacket 62 of the second pair of wires 58. Indeed, the nonconductive jacket 62 may include polymeric materials that are substantially nonconductive. That is, the nonconductive jacket 62 may be formed from one or more polymers that are capable of electrically insulating the second conductive polymeric jacket 262 from other electrically conductive materials within the sensor cable 16. As an example, the nonconductive jacket 62 may include any flexible, nonconductive polymeric material such as polyvinylchloride (PVC), polyolefins (e.g., polyethylene, polypropylene), polyamides (e.g., nylon-6), synthetic or natural elastomers (e.g., neoprene), various other thermoplastics (e.g., thermoplastic chlorinated polyethylene (CPE)), or any combination thereof. However, in other embodiments, such as illustrated in FIG. 25, the second conductive polymeric jacket 262 may not be surrounded by the nonconductive jacket 62. Additionally, in such an embodiment, the second conductive polymeric jacket 262 and the main conductive jacket 260 may be in contact.

In the embodiment illustrated in FIG. 24, the main conductive polymer jacket 260 and the second conductive polymer jacket 262 are separated the nonconductive jacket 62. As illustrated, the main conductive polymer jacket 260 may surround both of the pairs of wires 56, 58, which provides EMI/RFI for the first pair of wires 56 and an additional level of EMI/RFI shielding for the second pair of wires 58. In a similar manner to the second conductive polymer jacket 262, the main conductive polymer jacket 260 may include one or more drain wires 282. The drain wires 282 may enable termination of the main conductive polymer jacket 260 at the bandage and/or connector side of the sensor cable 16. However, as noted above with respect to the second conductive polymer jacket 262, the main conductive polymer jacket 260 may be terminated without using the drain wires 282, as illustrated in FIG. 25. The main conductive polymer jacket 260 and the second conductive polymer jacket 262 may also be separated by one or more cords 284 that are made of a fiber material 286. The cords 284 may provide support for and maintain the position of the wires 56, 58 within the sensor cable. As an example, the fiber material 286 may include cotton, wool, silk, polyester, nylon, or other similar fabric materials. The components of the sensor cable 16 described above may all be enclosed by the main nonconductive jacket 54. The main nonconductive jacket 54 may be formed from electrically insulative polymer materials, such as those described above with respect to the nonconductive jacket 62. Generally, the main nonconductive jacket 54 may prevent electrical shorts from occurring. The main nonconductive jacket may also prevent the caregiver (e.g., technician, nurse, doctor) and the patient from being exposed to any electrically conductive materials.

The embodiments of the sensor cable 16 illustrated in FIGS. 24 and 25 may be constructed according to the desired end use of the cable (e.g., pulse oximetry, electrocardiography), the materials available for the construction process, production costs, or similar considerations. FIG. 26 is a process flow diagram illustrating a method 290 for constructing the embodiments of the sensor cable 16 depicted in FIGS. 24 and 25. Further, it should be noted that certain of the steps of the method 290 may be performed to construct similar cable embodiments, such as cables having a conductive polymer only in the main conductive jacket 260, or only in the second conductive polymer jacket 262. Such embodiments are discussed in detail below with respect to FIGS. 27-29.

The method 290 begins with obtaining the materials used to produce either or both of the conductive polymer jackets 260, 262, obtaining the pairs of wires 56, 58, the nonconductive materials for the insulating jackets 54, 62, drain wires 282, 276, and other materials that may be desirable for inclusion in the sensor cable 16 (block 292). After the materials are obtained, the second pair of wires 58 (i.e., the twisted pair) may be surrounded by the second conductive polymer jacket 262 (block 294). As an example, the materials of the second conductive polymer jacket 262 may be combined (e.g., blended, mixed, compounded) and extruded, molded, or shrink-wrapped over the second pair of wires 58. Indeed, any jacketing procedure known in the art may be used in accordance with the present disclosure.

To generate the sensor cable 16 embodiment illustrated in FIG. 24, the second pair of wires 58, which have been jacketed with the second conductive polymer jacket 262, are then surrounded by the nonconductive jacket 62 (block 296). For example, the nonconductive polymers that are used to produce the nonconductive jacket 62 may be extruded, molded, or shrink-wrapped over the second conductive polymer jacket 262. However, as noted above, to produce the embodiment of the sensor cable 16 illustrated in FIG. 25, the acts represented by block 296 may not be performed.

After the second pair of wires 58 have been shielded and, in some embodiments, insulated, the first pair of wires 56, as well as the fiber cords 284, and any other wiring, are provided and disposed proximate the second pair of wires 58 (block 298). The resulting arrangement is then jacketed with the main conductive polymer jacket 260 (block 300). For example, as above, the main conductive polymer jacket 260 may be extruded, molded, or shrink-wrapped over the sensor wires, cords, and other sensor materials. The main conductive polymer jacket 260 is then covered with the main nonconductive jacket 54 (block 302).

As noted above, the conductive polymer embodiments disclosed herein may be used in lieu of, or in addition to, other shielding features, such as conductive strands of wire, metallic meshes, or the like. FIGS. 27 and 29 depict embodiments of such approaches. The embodiment of the sensor cable 16 illustrated in FIG. 27 has a fully metallic EMI/RFI shield 306 used as the main conductive jacket (i.e., in the place of the main conductive polymer jacket 260). The fully metallic EMI/RFI shield 306 may include a plurality of electrically conductive wire strands, a continuous sheath of metal (i.e., a cylindrical structure), a metallic mesh, or similar structure. The metal used in the shield 306 may include any conductive metal used for EMI/RFI shielding known in the art, such as copper, nickel, gold, and so on. Moreover, while the embodiment of the sensor cable 16 depicted in FIG. 27 illustrates the fully metallic EMI/RFI shield 306 as being separated from the second conductive polymer jacket 262 by the nonconductive jacket 62, in some embodiments, the fully metallic EMI/RFI shield 306 and the second conductive polymer jacket 262 may be in electrical contact.

FIG. 28 illustrates an embodiment of a method 308 for producing the sensor cable 16 of FIG. 27. Because the sensor cable 16 of FIG. 27 includes many of the same elements as the sensor cable 16 of FIG. 24, many of the steps of method 308 may be similar or the same as certain steps in method 290 of FIG. 26. Accordingly, those steps will be referred to using the same reference numerals as those used in FIG. 26. At the onset of method 308, the materials used to construct the sensor cable 16 of FIG. 27, such as jacketed wires, the conductive polymer, the nonconductive polymer(s), and the fully metallic shielding materials may be obtained (block 310).

After the suitable materials are obtained, acts in accordance with blocks 294-298 may be performed as described above with respect to FIG. 26. Thus, the second pair of wires 58 may then be surrounded by the conductive polymer to form the second conductive polymer jacket 262 (block 294). The second conductive polymer jacket 262 may then be covered by the nonconductive jacket 62 (block 296). After the second pair of wires 58 is insulated, the first pair of wires 56, the fiber cords 284, and other sensor materials are disposed proximate the second pair of wires 58 (block 298).

After the internal components of the sensor cable 16 are situated in their desired arrangement, the metallic material may be placed around the arrangement to form the fully metallic EMI/RFI shield 306 (block 312). For example, in embodiments where the metallic material is a plurality of conductive wire strands, the strands may be braided or twisted about the jacketed wires. In embodiments where the metallic material is a metal mesh or a continuous metallic sheath, the metal may be wrapped around the internal components of the sensor cable 16. Indeed, any manner of disposing fully metallic shielding about cable components known in the art may be used in accordance with certain of the present embodiments. The fully metallic EMI/RFI shield 306 may then be surrounded by the main nonconductive jacket 54 (block 314).

While FIG. 27 depicts an embodiment of the sensor cable 16 having the fully metallic EMI/RFI shield 306 as the main EMI/RFI shield, FIG. 29 depicts an embodiment of the sensor cable 16 having a fully metallic EMI/RFI shield 318 disposed about the second pair of wires 58. Specifically, the embodiment of the sensor cable 16 illustrated in FIG. 29 includes the fully metallic EMI/RFI shield 318 disposed about the second pair of wires 58 and the main conductive polymer jacket 260 used as the main EMI/RFI shield for the sensor cable 16. Such an embodiment may be formed as a result of certain manufacturing processes, such as in remanufacturing processes where the second pair of wires 58, and the shielding/jacketing surrounding the second pair of wires 58, are determined to be suitable for inclusion in a remanufactured cable. Indeed, such methods of remanufacturing cables and bandage sensors that may use such cables are discussed in detail below with respect to FIGS. 37-40.

The embodiment of the sensor cable 16 illustrated in FIG. 29 may be produced from new and/or refurbished materials using a method 320 illustrated in FIG. 30. Because the sensor cable 16 of FIG. 29 includes many of the same elements as the sensor cable 16 of FIG. 27, many of the steps of method 320 may be similar or the same as certain steps of methods 290 and 308 of FIGS. 26 and 28, respectively. Accordingly, those steps will be referred to using the same reference numerals as those used in FIGS. 26 and/or 28. At the onset of method 308, the materials used to construct the sensor cable 16 of FIG. 29, such as jacketed wires, the conductive polymer, the nonconductive polymer(s), and the fully metallic shielding materials may be obtained (block 310).

After the suitable materials are obtained, the metallic material may be placed around the second pair of wires 58 to form the fully metallic EMI/RFI shield 318 (block 322). For example, the fully metallic EMI/RFI shield 318 may be disposed about the second pair of wires 58 in a similar manner to that described above with respect to block 312 of method 310. The fully metallic EMI/RFI shield 318 may then be surrounded by the nonconductive jacket 62 (block 324). After the second pair of wires 58 are insulated, the first pair of wires 56, the fiber cords 284, and other sensor cable materials are disposed proximate the second pair of wires 58 (block 298). The conductive polymer may then be disposed (e.g., extruded, molded, shrink-wrapped) over the resulting arrangement to form the main conductive polymer jacket 260 (block 300). The main nonconductive jacket 302 may then be disposed about the main conductive polymer jacket 260 (block 302) to form the sensor cable 16 of FIG. 29.

As noted above, the bandage sensor 14 discussed with respect to FIGS. 1-15 and the sensor cable 16 discussed with respect to FIGS. 1 and 24-30 may be manufactured from new, refurbished, and/or used materials. Indeed, the present embodiments provide various methods for remanufacturing bandage sensors and sensor cables in accordance with the embodiments discussed above. For example, FIG. 31 illustrates a generalized sensor remanufacturing method, FIGS. 32-36 illustrate bandage sensor remanufacturing methods for integrating or removing ECATT layers, FIGS. 37 and 39 each illustrate a sensor cable remanufacturing method, and FIGS. 38 and 40 each illustrate an embodiment of a method for replacing a used sensor cable with a new sensor cable, wherein either of the used or the new sensor cable includes a conductive polymer EMI/RFI shielding jacket.

Referring now to FIG. 31, an embodiment of a method 330 for remanufacturing a medical sensor, such as the bandage sensor 14, is illustrated. The method begins with obtaining a used sensor (block 332). The used sensor may be a single-use medical sensor (i.e., for use on a single patient) or may be a reusable sensor. The sensor may be obtained, as an example, by a technician or similar manufacturing personnel. The technician may inspect and/or test the operation of the sensor (block 334). As an example, in embodiments where the sensor is a pulse oximetry sensor, the testing may include testing the operation and accuracy of the emitter, the detector, the sensor cable, the cable connector, and any other electronic features of the sensor, such as a memory disposed within the connector.

After the sensor has been inspected and tested, the technician may determine whether it is appropriate to remanufacture the sensor (query 336). In embodiments where remanufacture is not appropriate, the used sensor may be discarded (block 338). For example, one or more features of the used sensor may be inoperative, such as the monitoring features, the cable, and so on. Depending on the degree to which the sensor may be inoperative, it may no longer be cost-effective to remanufacture, and the sensor may be discarded. Conversely, in embodiments where it is determined that at least a portion of the sensor is suitable for remanufacturing, the sensor may be remanufactured according to certain remanufacturing processes (block 340). Embodiments of such remanufacturing processes are discussed below. After the sensor has been remanufactured, the sensor is then packaged and sterilized (block 344). The sensor may then be sent to a medical facility for use.

Moving now to FIG. 32, an embodiment of a method 350 for producing the sensor bandage 14 having the ECATT layer 48 as a Faraday shield from a used sensor bandage is illustrated. The method 350 may be performed independently or in conjunction with the method 330 of FIG. 31. For example, the method 350 may correspond to the acts represented by block 340 of method 330. In either case, the used sensor bandage may be determined to include reusable parts, such as the optics (e.g., the emitter, detector) and/or the sensor cable. It should be noted, however, that in embodiments where any one of these re-usable components is not suitable for further use, it may be replaced with a traditional replacement part, or may be replaced with features corresponding to aspects of the present disclosure (e.g., the sensor cable 16 of FIGS. 24, 25, 26, 29).

The method 350 begins with removing the optical assembly and the sensor cable (block 352). As noted above, the optical assembly may include the emitter (e.g., the emitter 26) and the detector (e.g., the detector 28), and the sensor cable may be a traditional sensor cable or the sensor cable 16 of FIG. 24, 25, 26, or 29. As an example, the optical assembly and the sensor cable may be removed from the bandage sensor by opening the housing of the sensor (e.g., one or more laminated, flexible layers or a plastic or over molded housing) and removing the optics and the cable. Because the detector may be shielded by a fully metallic Faraday shield (e.g., a copper mesh and/or a copper sheath), certain features of the sensor cable (e.g., a drain wire) may be soldered to the Faraday shield. Accordingly, the sensor cable may be detached from the Faraday shield, and the Faraday shield may be discarded, recycled, or repurposed.

Once the optical assembly and the sensor cable have been removed, the optical assembly and the sensor cable may be cleaned (block 354). As an example, the active faces of the emitter and/or the detector may be cleaned with a cleaning solution, or a cloth having a cleaning solution, and dried. It will be appreciated that the manner of drying the emitter and the detector may be such that no dust, lint or other small particulates are left of the active face of either. The outer jacket of the sensor cable may be cleaned and/or re-painted such that the sensor has a substantially new appearance. In embodiments where the connector includes a memory module, the module may be cleared of any patient historical data. Further, the connector of the sensor cable may be cleaned, such as by removing particulates that may be proximate the pins of the connector. This cleaning may help to ensure proper attachment to a monitor and acceptable performance of the remanufactured sensor. In certain embodiments, the sensor cable may also be re-soldered to the optics to ensure a proper connection. Furthermore, in embodiments in which it may be desirable to discard and replace any of these features, the sensor cable may be re-soldered to a new emitter and/or detector, or the emitter and the detector may be soldered to a new cable.

After the optics and the sensor cable are ready for integration into a new sensor, the top release liner 144 may be removed from the laminate assembly 44 (block 356). The emitter and the detector may then be disposed on the laminate assembly 44 (block 358). For example, the emitter and the detector may be aligned with the first and second optical windows 92, 94, respectively. As illustrated in FIG. 4, the emitter may be disposed directly on the first surface 100 of the main nonconductive support layer 46, and the detector may be disposed directly on the first side 104 of the nonconductive adhesive layer 50. Before, after, or during the acts represented by block 358, the termination features of the sensor cable may be attached to the ECATT layer 48 of the laminate assembly 44 (block 360). For example, a drain wire of the sensor cable may be adhesively secured to the ECATT layer 48. The resulting configuration may be as illustrated in FIG. 2 or 18-21. Indeed, the ECATT layer 48, as discussed above, may have any shape, size, or configuration that enables the ECATT layer 48 to shield the detector from EMI/RFI while allowing termination of the sensor cable.

After the optical assembly and the sensor cable are suitably placed on the laminate assembly 44, the laminate assembly 44 is folded over the optics and the cable to form the sensor body 40 (block 362). For example, as illustrated with respect to the folds in the main nonconductive support layer 46 in FIG. 4, the left and right extents of the laminate assembly may be folded over the optics and the cable. This folding may result in the detector being surrounded by the ECATT layer 48 and the nonconductive adhesive layer 50, which provides 360° shielding for the detector and 360° termination for the cable. After the sensor body 40 is formed, the sensor bandage top assembly 70 may be disposed on the non-patient contacting surface 74 of the sensor body 40, as illustrated in FIG. 3, to produce the bandage sensor 14 (block 364).

While the method 350 described above may be performed to replace all of the sensor components other than the electronics, it may be desirable to retain and re-use other features of the sensor. For example, it may be desirable to retain the outer layers of the sensor body 40, which may correspond to the main nonconductive support layer 44. Indeed, it may be desirable to simply replace the fully metallic Faraday shield of a used bandage sensor with the ECATT layer 48 described above. Accordingly, FIG. 33 illustrates an embodiment of a method 370 for remanufacturing a sensor to replace an existing Faraday shield, such as a metal mesh or sheath, with an electrically conductive transfer tape. Indeed, the method 370 may generally correspond to the acts represented by block 340 of method 330.

The method 370 includes removing the used sensor bandage layer (e.g., layer 24 or assembly 70) from the sensor body 40 (block 372). For example, it may be desirable to remove any layer that has come in contact with a patient. In some embodiments, the bandage top assembly 70 may be removed by pulling the bandage top assembly 70 away from the sensor body 40, the two of which may be adhesively coupled. In certain embodiments, it may also be desirable to remove the patient-contacting adhesive layer 90. However, as described below, in some embodiments the used patient-contacting adhesive layer 90 may simply be covered with a fresh patient-contacting adhesive layer 90. In certain embodiments, the fresh patient-contacting adhesive layer 90 may extend proud of the sensor body 40 onto the surface 42 of the top bandage assembly 70, or may extend to the perimeter of the surface 42.

Once the used sensor body 40 has been isolated from the bandage top assembly 70, the sensor body 40 may be opened, and the fully metallic Faraday shield and insulating layer may be removed (block 374). For example, the sensor body 40 may be opened with a cutting tool and carefully pulled apart to expose the emitter, the detector, the fully metallic Faraday shield, among others. The Faraday shield and insulating layer between the Faraday shield and the detector may be adhesively secured to the detector. Therefore, the fully metallic Faraday and the insulating layer may simply be pulled away from the detector to remove them. With the optical assembly being at least partially isolated from the sensor body 40, the emitter, the detector, and the sensor cable may be cleaned (block 376). For example, these components may be cleaned as set forth above with respect to block 354 of method 350. Indeed, after the detector has been at least partially pulled away from the sensor body 40, the ECATT layer 48 and the nonconductive adhesive layer 50 may be disposed about the detector (block 378). For example, the ECATT layer 48 and the nonconductive adhesive layer 50 may be secured to one another, and then adhesively secured to the detector or the main nonconductive support layer 46 which, when folded back over the detector, will cause the ECATT layer 48 to shield the detector.

After the ECATT layer 48 and the nonconductive adhesive layer 50 are in place, the sensor body 40 may be re-sealed (block 380). For example, an adhesive may be applied to the main nonconductive support layer 46 to re-seal the opening formed at block 374. In other embodiments, the main nonconductive support layer 46 may include one or more adhesive surfaces that allow it to be re-sealed, forming the remanufactured sensor body 40.

Before, after, or while the sensor body 40 is re-sealed, a new patient contacting adhesive layer 90 may be disposed on the sensor body 40 (block 382). For example, as noted above, in certain embodiments, the patient-contacting adhesive layer 90 may be removed in accordance with the acts represented by block 372. Accordingly, the acts represented by block 382 may act to replace the removed adhesive layer. However, as illustrated, the used patient-contacting adhesive layer 90 may be covered with a new patient-contacting adhesive layer 90 (block 382). Before, after, or during these acts, a new bandage top assembly 70 may be disposed on the sensor body 40 (block 364), as described above.

Figure 34:
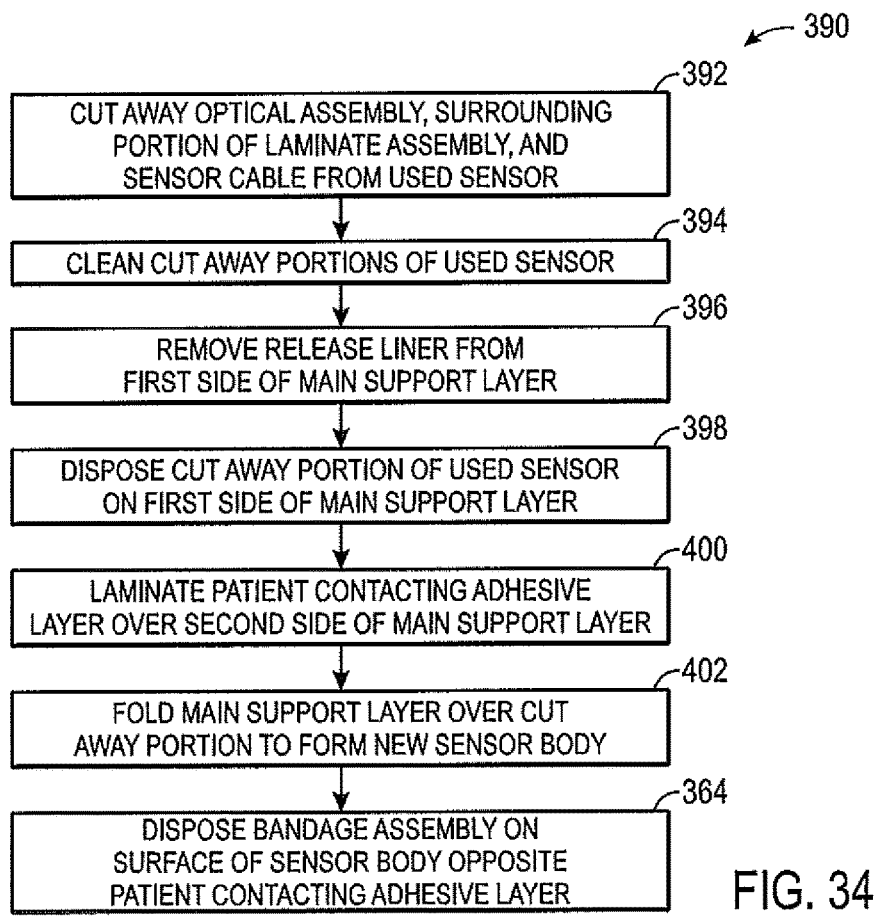
FIG. 34 is a process flow diagram illustrating an embodiment of a method for remanufacturing a bandage sensor in a manner that retains an electrically conducive adhesive transfer tape layer as a Faraday shield, in accordance with an aspect of the present disclosure.

While the remanufacturing embodiments described above may be directed toward remanufacturing sensors having fully metallic Faraday shields, it may be desirable to remanufacture used sensors that have electrically conductive transfer tape Faraday shields. Accordingly, it may be desirable to retain at least a portion of the sensor that contains the electrically conductive transfer tape Faraday shield. FIG. 34 illustrates an embodiment of one such method 390 for remanufacturing a sensor having an electrically conductive transfer tape Faraday shield. The method 390 may begin by cutting the optical assembly, a portion of the laminate assembly 44 surrounding the optical assembly, and the sensor cable 16 from the used sensor (block 392). For example, in one embodiment, the detector area 200 illustrated in FIG. 8 may be cut away, along with the sensor portions surrounding the emitter 26 and the sensor cable 16, from the remaining portions of the bandage sensor 14. In another embodiment, the middle portion of the bandage sensor 14 corresponding to the sensor body 40 may be cut away from the outer portions of the bandage layer 24.

After the portions that are cut away from the sensor, the cut away portions may then be cleaned (block 394). For example, the portions of the patient-contacting adhesive layer 90 disposed proximate the active faces 96, 98 of the emitter 26 and the detector 28 may be cleaned. Additionally, portions of the sensor cable 16 may be cleaned as set forth above. For example, the main jacket 54 and the connector 18 may be cleaned and the memory module 20 may be cleared of patient historical data. After the emitter 26, the detector 28, the sensor cable 16 and other sensor components that have been cut away from the bandage sensor 14, the main nonconductive support layer 46 may be disposed over the optical assembly and surrounding laminate layers.

Specifically, a release liner may be removed from the first side of the main nonconductive support layer (block 396), and the cut away portion may be disposed on the uncovered portion of the main nonconductive support layer 46 (block 398). A new patient-contacting adhesive layer 90 may be laminated on the main nonconductive support layer 46 (block 400) before, after, or while the main nonconductive support layer 46 is laminated with the cut away and cleaned sensor portions. However, it should be noted that in embodiments where the sensor body 40 is cut away from the bandage sensor 14 such that the sensor body 40 is completely intact, the acts according to blocks 396 and 398 may not be performed, and a new patient-contacting adhesive layer 90 may be simply laminated over the used patient-contacting adhesive layer 90. In such an embodiment, this may form a new sensor body 40.

After the laminations above are completed, the main nonconductive support layer 46 may be folded over the cut away portions of the sensor to form the new sensor body 40 (block 402). It should be noted, however, that the main nonconductive support layer 46, in some embodiments, may be folded over the cut away portions immediately after they are placed on the main nonconductive support layer 46. After the new sensor body is formed, the bandage top assembly 70 may be laminated over the sensor body 40 on the non-patient contacting surface 74 to form the remanufactured bandage sensor 14 (block 364).

Figure 35:
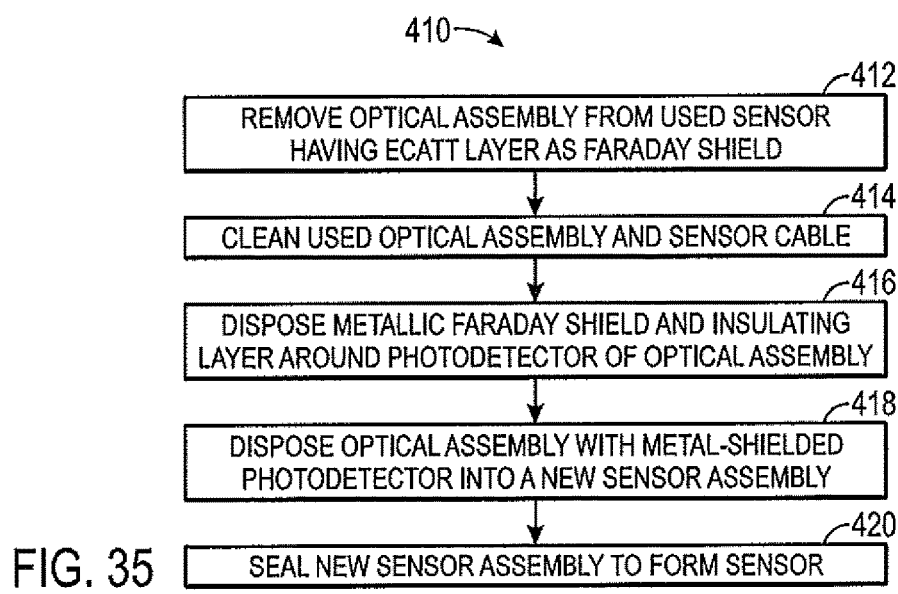
FIG. 35 is a process flow diagram illustrating an embodiment of a method for remanufacturing a bandage sensor in a manner that replaces an electrically conductive adhesive transfer tape layer with a fully metallic Faraday shield, in accordance with an aspect of the present disclosure.

The embodiments described above may be directed towards situations where it may be desirable to use sensor bandages having ECATT Faraday shields. However, it may also be desirable to remanufacture sensors in a manner that replaces the ECATT Faraday shields described herein with other shielding technologies, such as metallic meshes, metallic sheaths, metallic wire strands, and so on. Indeed, in accordance with certain embodiments described herein, the ECATT layer 48 may be replaced by simply disposing the drain wire 60 in a region proximate the detector 28 to reduce EMI experienced by the detector 28. FIG. 35 illustrates an embodiment of one such method 410 for remanufacturing a sensor, such as bandage sensor 14, to replace the ECATT layer 48 with a fully metallic Faraday shield, such as a mesh or another Faraday shield consisting essentially of, or containing a large portion of, a conductive metal. The method 410 may begin with removing the optical assembly from the sensor body 40 (block 412). For example, the emitter 26, the detector 28, and, in certain embodiments, the sensor cable 16 may be cut away from the sensor body 40.

After the optical assembly and the sensor cable 16 have been removed, they may be cleaned (block 414). For example, the active faces of the emitter 26 and the detector 28 may be wiped clean, and the sensor cable 16 may be reconditioned according to any suitable protocol. Indeed, in certain embodiments, such as when the sensor cable 16 includes one or more conductive polymer jackets, the sensor cable 16 may also be replaced. Once the desired components have been cleaned, a new, fully metallic Faraday shield may be disposed on or about at least the detector 28 (block 416).

Moreover, in embodiments where the sensor cable includes a drain wire, the drain wire may be soldered to the fully metallic Faraday shield.

After the components have been removed, cleaned, reconditioned, and shielded as desired, the optics (with the detector having a fully metallic Faraday shield) and the cable may be disposed within a new sensor assembly, such as one or more layers that are adapted to surround the optics and the cable as all or a part of the remanufactured sensor (block 418). The remanufactured sensor may then be sealed (block 420) to form the sensor. Of course, the process described above may include one or more additional steps as may be desired to produce a given remanufactured sensor, such as the addition of proprietary components, the addition of new adhesive layers, and so forth.

Figure 36:
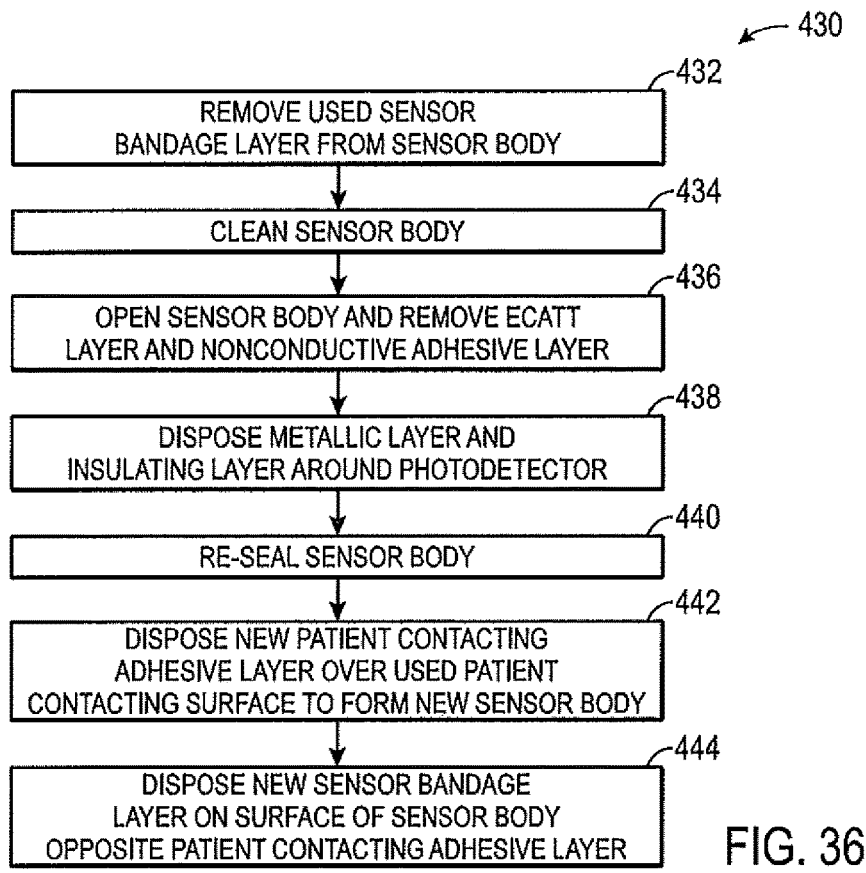
FIG. 36 is a process flow diagram illustrating an embodiment of a method for remanufacturing a bandage sensor in a manner that replaces an electrically conductive adhesive transfer tape layer with a fully metallic Faraday shield, in accordance with an aspect of the present disclosure.

Furthermore, the remanufacturing process to replace the ECATT layer 48 may simply replace the ECATT layer 48 and the remaining portions of the sensor body 40 may be re-used. FIG. 36 illustrates an embodiment of such a method 430. The method 430 includes removing the used sensor bandage layers (e.g., some or all of the bandage top assembly 70) (block 432). The sensor body 40 may then be cleaned to prevent the internal components of the sensor from being exposed to external contaminants (block 434). However, in certain embodiments, the cleaning step may be performed after certain of the steps described below.

The sensor body 40 may then be opened, and the ECATT layer 48 and, in certain embodiments, the nonconductive adhesive layer 50 are removed (block 436). For example, because the ECATT layer 48 and the nonconductive adhesive layer 50 are adhesively secured to the detector 28, they may be simply pulled away from the detector 28. The fully metallic Faraday shield and, in some embodiments, an insulative layer, may then be placed about the detector 28 (block 438). The sensor body may then be re-sealed (block 440). For example, additional adhesive may be applied to the sensor body for re-sealing, or the adhesive nature of certain of the sensor body layers may allow the sensor body to be re-sealed by placing the layers in contact with one another and applying pressure. A new patient-contacting layer may then be applied to the re-sealed sensor body (block 442). One or more new bandage layers may also be applied to the re-sealed sensor body (block 444).

Figure 37:
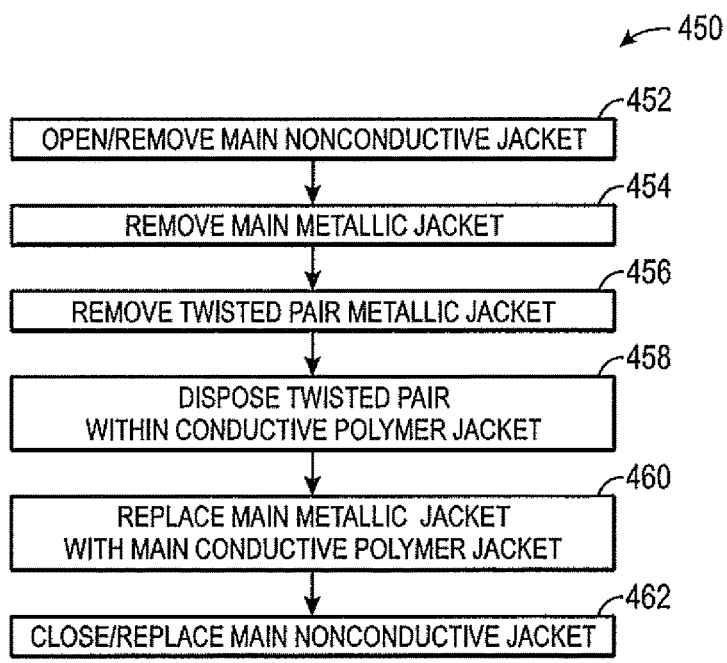
FIG. 37 is a process flow diagram illustrating an embodiment of a method for remanufacturing a sensor cable in a manner that replaces a fully metallic EMI/RFI shield with a conductive polymer, in accordance with an aspect of the present disclosure.

While the remanufacturing methods described above are directed toward the remanufacture of a medical sensor, it may be desirable to also remanufacture the sensor cable. In other embodiments, only the sensor cable may be remanufactured. Indeed, in embodiments where the cable may be used for other medical purposes, or as an extension cable, it may be desirable to remanufacture the cable to include or remove one or more conductive polymer jackets. FIG. 37 illustrates an embodiment of a method 450 for remanufacturing a cable, such as a pulse oximetry sensor cable, to include one or more conductive polymer EMI/RFI shielding jackets. To facilitate discussion, the method 450 will be described in the context of producing the sensor cable 16 from a sensor cable having traditional shielding features. The method 450 includes opening/removing the main nonconductive jacket of the cable (block 452). For example, the main jacket may be cut open and peeled away from the remaining components of the sensor cable, or a stripping device may remove the jacket either automatically or as a result of acts performed by a technician.

The main metallic shielding jacket may then be removed (block 454). For example, in embodiments where the fully metallic shielding jacket includes a plurality of wire strands, the strands may be separated and removed, or pulled at their ends away from the remaining components of the sensor cable. After the fully metallic jacket is removed, any wires that are grouped and separately shielded may be identified, and their shields removed (block 456). In the context described above with respect to FIG. 29, the fully metallic EMI/RFI shield 318 of the second pair of wires 58 may be removed. In this way, all of the wires of the sensor cable are de-shielded. The removed metal may be discarded, recycled, or repurposed for another use.

After the fully metallic shield has been removed from the second pair of wires 58, a conductive polymer may be extruded or otherwise disposed over the second pair of wires 58 to produce the second conductive polymer jacket 270 (block 458). That is, the second pair of wires 58 may be disposed within the second conductive polymer jacket 262. Similarly, after all of the internal wires, packing components, and so forth are in place, a conductive polymer may be extruded or otherwise disposed over the internal components to produce the main conductive polymer jacket 260 (block 460). As noted above, the main conductive polymer jacket 260 may include similar, the same, or different materials than the materials used for the second conductive polymer jacket 262. After shielding the internal components of the sensor cable, the main nonconductive jacket 54 may be disposed over the main conductive polymer jacket 260 and closed (block 462). For example, in some embodiments, the main nonconductive jacket 54 may be closed using heat, an adhesive, a sealing composition, or the like. In other embodiments, such as when it may be desirable to replace the main nonconductive jacket, a nonconductive polymer may be extruded over the main conductive polymer jacket 260 to produce the sensor cable 16.

Figure 38:
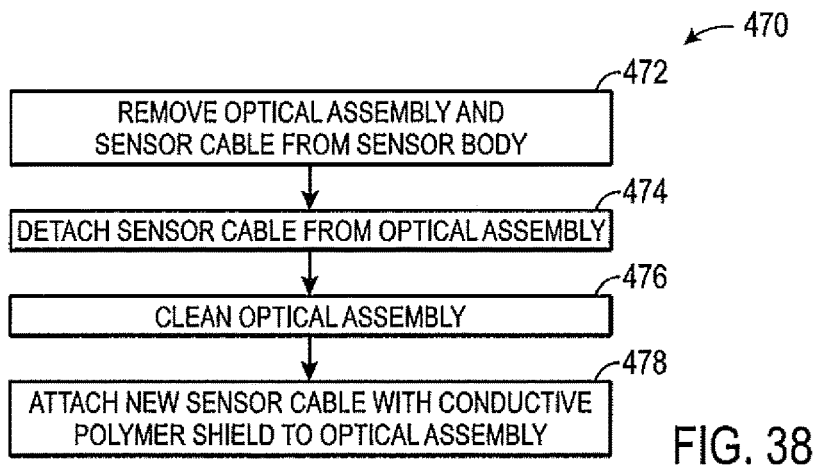
FIG. 38 is a process flow diagram illustrating an embodiment of a method for remanufacturing a bandage sensor in a manner that replaces a used sensor cable having a fully metallic EMI/RFI shield with a sensor cable having at least one conductive polymer EMI/RFI shield, in accordance with an aspect of the present disclosure.

While the method 450 described above may be desirable in situations where it is desirable to re-manufacture a sensor cable, it may be desirable, during the remanufacturing of a sensor, to replace a used cable having fully metallic shielding features with the sensor cable 16 having at least one conductive polymer jacket. For example, it may be desirable to replace an existing sensor cable with any of the embodiments of the sensor cable 16 discussed with respect to FIG. 24, 25, 27, or 29. FIG. 38 illustrates an embodiment of such a method 470. Further, it should be noted that the method 470 may be performed alone or in conjunction with other of the sensor remanufacture embodiments disclosed herein.

The method 470 may begin by removing the optical assembly (e.g., the emitter 26 and the detector 28) and the sensor cable from the sensor body (block 472). For example, the sensor body, which may be a portion of the used sensor, may be opened and the optical assembly and the cable pulled away from the sensor body. The used sensor cable may then be removed from the emitter 26 and the detector 28 (block 474). For example, the solder coupling the used sensor cable to the emitter 26 and the detector 28 may be heated and pulled apart. In another embodiment, the solder may be cut to de-couple the emitter 26 and the detector 28 from the used sensor cable.

After the emitter 26 and the detector 28 have been de-coupled from the used sensor cable, they may be cleaned (block 476). A new sensor cable 16 having at least one conductive polymer shield may then be attached to at least the emitter 26 and the detector 28 (block 478). For example, the first pair of wires 56 may be soldered to a pair of leads of the emitter 26. Likewise, the second pair of wires 58 may be soldered to a pair of leads of the detector 28. The emitter 26, the detector 28, and the new sensor cable 16 may then be integrated into a new or remanufactured sensor, such as a pulse oximetry bandage sensor in accordance with the disclosed embodiments.

The embodiments described above with respect to the remanufacture of the sensor cable may be performed in situations where it is desirable to have a sensor cable with one or more conductive polymer jackets for EMI/RFI shielding. However, it may be desirable to remanufacture or replace such sensor cables such that a new or remanufactured sensor has a sensor cable with only fully metallic shielding jackets. In other embodiments, it may be desirable to only replace certain of the conductive polymer jackets and retain others. Such embodiments are described with respect to FIGS. 39 and 40.

Figure 39:
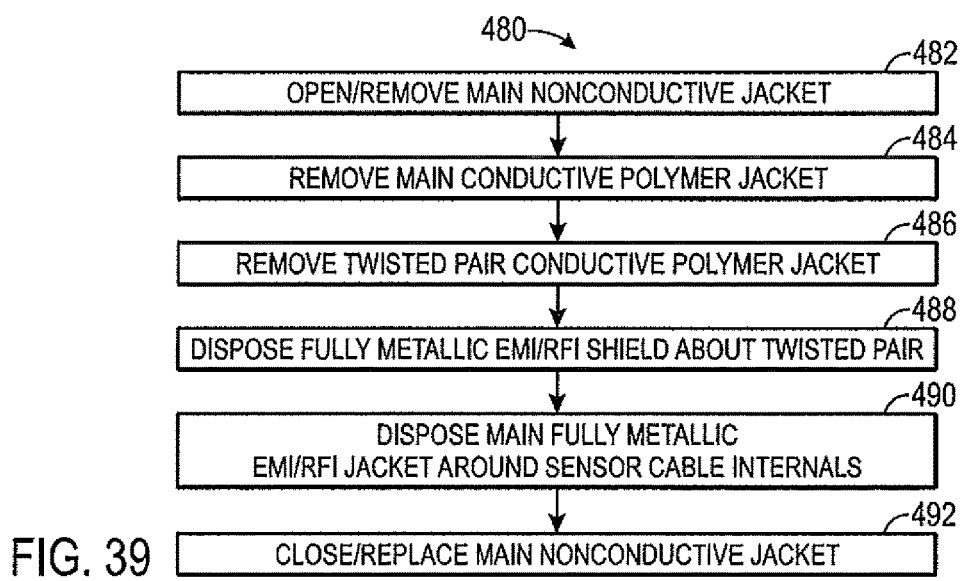
FIG. 39 is a process flow diagram illustrating an embodiment of a method for remanufacturing a sensor cable in a manner that replaces a conductive polymer EMI/RFI shield with a fully metallic EMI/RFI shield, in accordance with an aspect of the present disclosure.
Figure 40:
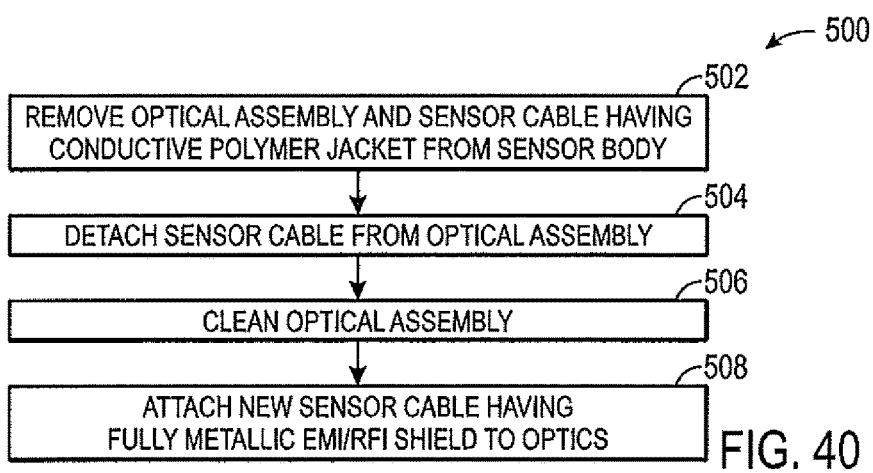
FIG. 40 is a process flow diagram illustrating an embodiment of a method for remanufacturing a bandage sensor in a manner that replaces a used sensor cable having a conductive polymer EMI/RFI shield with a sensor cable having at least one fully metallic EMI/RFI shield, in accordance with an aspect of the present disclosure.

Specifically, FIG. 39 illustrates an embodiment of a method 480 for remanufacturing a sensor cable having a conductive polymer jacket with a fully metallic EMI/RFI shield. Indeed, while the method 480 is described in the context of replacing all of the conductive polymer jackets that may be present in a sensor cable with fully metallic jackets, it should be noted that the selective replacement of one or more conductive polymer jackets with a fully metallic jacket is also presently contemplated, as illustrated with respect to FIGS. 27 and 29. The method 480 may begin by opening/removing the main nonconductive jacket of the cable (block 482). For example, the main jacket may be cut open and peeled away from the remaining components of the sensor cable, or a stripping device may remove the jacket either automatically or as a result of acts performed by a technician.

The main conducive polymer jacket 260 may then be removed (block 484). For example, the conductive polymer jacket 260 may be cut and peeled away from the internal components of the sensor cable 16. After the conductive polymer jacket 260 is removed, any wires that are grouped and separately shielded may be identified, and their shields removed (block 486). For example, the second conductive polymer jacket 262 of the second pair of wires 58 may be removed. In this way, all of the wires of the sensor cable are de-shielded. The removed conductive polymers may be discarded, recycled, or repurposed for another use. Again, in certain embodiments, only a portion of the conductive polymer jackets may be removed.

After the second conductive polymer jacket 262 has been removed from the second pair of wires 58, a fully metallic EMI/RFI shield may be disposed over the second pair of wires 58 (block 488). For example, in embodiments where the jacket is a plurality of conductive wire strands, the wire strands may be braided, intertwined, or the like, and disposed about the second pair of wires 58. In other embodiments, such as when the fully metallic EMI/RFI shield is a sheath or mesh, the second pair of wires 58 may be slid inside the sheath or mesh, or the sheath or mesh may be wrapped around the second pair of wires 58.

Similarly, after all of the internal wires, packing components, and so forth are in place, a fully metallic EMI/RFI shield may be similarly disposed over the internal components to produce the main fully metallic EMI/RFI shield (block 490). The main fully metallic EMI/RIF shield may include similar, the same, or different materials than the metal used for the jacket disposed around the second pair of wires 58. After shielding the internal components of the sensor cable, the main nonconductive jacket 54 may be disposed over the main fully metallic EMI/RFI shield and closed (block 492). For example, in some embodiments, the main nonconductive jacket 54 may be closed using heat, an adhesive, a sealing composition, or the like. In other embodiments, such as when it may be desirable to replace the main nonconductive jacket, a nonconductive polymer may be extruded over the main fully metallic EMI/RFI shield to produce the remanufactured sensor cable.

As noted above, FIG. 40 illustrates a method 500 for replacing a sensor cable having one or more conductive polymer jackets with a sensor cable having one or more fully metallic shielding jackets. The method 500 may begin by removing the optical assembly (e.g., the emitter 26 and the detector 28) and the sensor cable 16 from the sensor body 40 (block 502). The sensor cable 16 may then be removed from the emitter 26 and the detector 28 (block 504). For example, the solder coupling the sensor cable 16 to the emitter 26 and the detector 28 may be heated and pulled apart. In another embodiment, the solder may be cut to de-couple the emitter 26 and the detector 28 from the sensor cable 16.

After the emitter 26 and the detector 28 have been de-coupled from the sensor cable 16, they may be cleaned (block 506). A new sensor cable having at least one fully metallic EMI/RFI shield may then be attached to at least the emitter 26 and the detector 28 (block 508). For example, the first pair of wires 56 may be soldered to a pair of leads of the emitter 26. Likewise, the second pair of wires 58 may be soldered to a pair of leads of the detector 28. The emitter 26, the detector 28, and the new sensor cable may then be integrated into a new or remanufactured sensor, such as a pulse oximetry bandage sensor in accordance with the disclosed embodiments.

Figure 41:
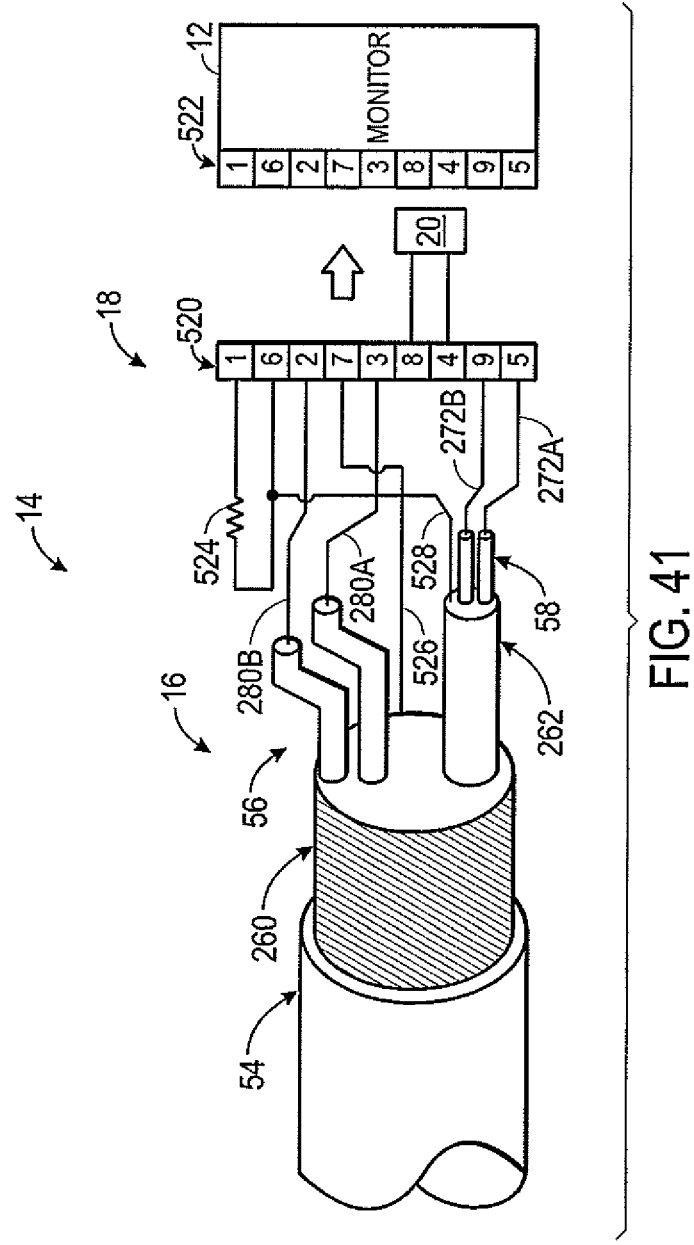
FIG. 41 is a diagrammatical illustration of an embodiment of a sensor cable having a conductive polymer EMI/RFI shield coupled to a connector.

An example configuration resulting from manufacturing or remanufacturing the bandage sensor 14 and/or the sensor cable 16 in accordance with the embodiments described above is illustrated with respect to FIG. 41. Specifically, FIG. 41 illustrates the manner by which the sensor cable 16, which may include one or more conductive polymer EMI/RFI shields, may attach to the connector 18. In FIG. 41, the connector 18 includes a pin configuration 520 that is compatible with a pin configuration 522 of the monitor 12. The sensor cable 16, as discussed above with respect to FIGS. 24, 25, 27, and 29, may include the first pair of wires 56, which may include conductors 280A and 280B (e.g., emitter lines), and the second pair of wires 58, which may include conductors 272A and 272B (e.g., detector lines).

In the provided example, the connector 18 includes a coded resistor 524 connected to pins 1 and 6 and configured to provide a coded resistor value to the monitor 12. The connector 18 also includes the memory unit 20, such as an erasable programmable read-only memory (EPROM) unit configured to store data, which is connected to pins 8 and 4. However, it should be noted that in certain embodiments, the connector 18 may include the memory unit 20 and not the coded resistor, or may include the coded resistor 524 and not the memory unit 20. For example, in embodiments where the bandage sensor 14 is an OXI-MAXT™ only pulse oximetry sensor, the connector 18 may include the memory unit 20 but not the coded resistor 524. In other embodiments, such as where the bandage sensor 14 represents an R-Cal-based sensor, the connector 18 may include the coded resistor 524 but not the memory unit 20.

The conductors 280A and 280B for the emitter 26 may pass through, or may be crimped to pins 3 and 2, respectively, of the pin configuration 520 so as to provide signals to and receive signals from the corresponding pins of the pin configuration 522 of the monitor 12 (i.e., pins 3 and 2). For example, the conductors 280A and 280B may provide emitter 26 control from a light drive (not shown) of the monitor 12. Likewise, the conductors 272A and 272B of the detector 28 may pass through, or may be crimped to pins 5 and 9, respectively, of the pin configuration 520 so as to provide signals to and receive signals from the corresponding pins of the pin configuration 522 of the monitor 12 (i.e., pins 5 and 9).

As noted above, the sensor cable 16 may include the main conductive polymer jacket 260 configured to provide EMI/RFI shielding for the entire sensor cable 16, and the second conductive polymer jacket 262 configured to provide additional EMI/RFI shielding for the conductors 272 and to prevent crosstalk between the conductors 272 and 280. As illustrated, the main conductive polymer jacket 260 terminates, via line 526, at pin 7 and the second conductive polymer jacket 262 terminates, via line 528, at pin 6. It should be noted that lines 526 and 528 may represent the jackets 260, 262 after unfolding from the sensor cable 16 and winding. In other embodiments, the lines 526 and 528 may represent drain wires, such as drain wires 282 and 276, respectively, of FIG. 24. In embodiments where the lines 526 and 528 represent the jackets 260, 262, the jackets 260, 262 may be grounded by crimping to pins 7 and 6, respectively, of the connector 18. Similarly, in embodiments where the lines 526 and 528 represent drain wires 282 and 276, respectively, they may be grounded by soldering or crimping to pins 7 and 6, respectively.

While the disclosure may be susceptible to various modifications and alternative forms, specific embodiments have been shown by way of example in the drawings and have been described in detail herein. However, it should be understood that the embodiments provided herein are not intended to be limited to the particular forms disclosed. Rather, the various embodiments may cover all modifications, equivalents, and alternatives falling within the spirit and scope of the disclosure as defined by the following appended claims.

What is claimed is:

1. A method of remanufacturing a used bandage-type medical sensor, comprising:
   obtaining the used bandage-type medical sensor, the used bandage-type medical sensor comprising an electrically conductive adhesive transfer tape (ECATT) layer disposed in a sensor body of the used bandage-type medical sensor and surrounding a detector of the used bandage-type medical sensor to shield the detector from EMI; and
   replacing a used patient-contacting adhesive bandage layer of the used bandage-type medical sensor with a new patient-contacting adhesive bandage layer.

2. The method of claim 1, wherein replacing the used patient-contacting adhesive bandage layer of the used bandage-type medical sensor with the new patient-contacting adhesive bandage layer comprises:
   removing the used patient-contacting adhesive bandage layer from a first side of a sensor body of the used bandage-type medical sensor; and
   securing the new patient-contacting adhesive bandage layer to the first side of the sensor body.

3. The method of claim 2, comprising securing a new additional patient-contacting adhesive layer to a second side of the sensor body, or to a used additional patient-contacting adhesive layer disposed on the second side of the sensor body, such that the used additional patient-contacting adhesive layer is completely covered by the new additional patient-contacting adhesive layer.

4. The method of claim 1, comprising replacing at least a portion of a used nonconductive support layer of the used bandage medical sensor with a new nonconductive support layer, and wherein replacing the used patient-contacting adhesive bandage layer of the used bandage medical sensor with the new patient-contacting adhesive bandage layer comprises securing the new patient-contacting adhesive bandage layer to the new nonconductive support layer.

5. The method of claim 4, wherein replacing at least the portion of the used nonconductive support layer comprises removing at least the portion of the used nonconductive support layer such that the detector remains shielded by the ECATT layer.

6. The method of claim 4, comprising replacing the ECATT layer with a metallic EMI shield, or with a drain wire positioned proximate the detector.

7. The method of claim 6, wherein replacing the ECATT layer with the metallic EMI shield includes removing the ECATT layer and disposing an insulating layer and the metallic EMI shield around the detector.

8. The method of claim 1, wherein the used bandage-type medical sensor is a used bandage-type pulse oximetry sensor, and the detector is a photodetector.

9. The method of claim 8, comprising retaining an optical assembly of the used bandage-type pulse oximetry sensor, the optical assembly having an emitter configured to transmit one or more wavelengths of light and the photodetector, wherein the photodetector is configured to receive the one or more wavelengths of light transmitted by the emitter, and the ECATT layer comprises a tape layer having a pressure-sensitive adhesive disposed on opposite sides and a conductive filler disposed in the adhesive.

10. The method of claim 9, wherein the ECATT layer fully covers the photodetector, is transparent with respect to the wavelengths of light emitted by the emitter and detected by the photodetector, and does not comprise an optical window.

11. The method of claim 10, wherein the used bandage-type pulse oximetry sensor comprises a sensor cable electrically coupled to the photodetector and the emitter, the sensor cable being configured to transmit signals between the used bandage-type pulse oximetry sensor and a pulse oximetry monitor, wherein the sensor cable comprises a drain wire that is terminated with the ECATT layer, and wherein the ECATT layer is isotropically conductive so as to form a 360° termination for the drain wire.

12. The method of claim 1, comprising:
   attaching a cable to the detector, the cable comprising a conductive jacketing having a conductive filler disposed within a polymer matrix, and wherein the conductive jacketing is configured to shield a conductor of the cable from EMI; and
   securing a cable termination of the cable to the ECATT layer.

13. The method of claim 1, wherein replacing the used patient-contacting adhesive bandage layer of the used bandage-type medical sensor with the new patient-contacting adhesive bandage layer comprises replacing the used patient-contacting adhesive bandage layer with more than one patient-contacting adhesive layer.

14. A method of remanufacturing a used bandage-type medical sensor, comprising:
   obtaining the used bandage-type medical sensor, the used bandage-type medical sensor comprising an electrically conductive adhesive transfer tape (ECATT) layer disposed in a sensor body of the used bandage-type medical sensor and surrounding a detector of the used bandage-type medical sensor to shield the detector from EMI, wherein the used bandage-type medical sensor is a used bandage-type pulse oximetry sensor, and the detector is a photodetector;

retaining an optical assembly of the used bandage-type pulse oximetry sensor, the optical assembly having an emitter configured to transmit one or more wavelengths of light and the photodetector, wherein the ECATT layer fully covers the photodetector, is transparent with respect to the wavelengths of light emitted by the emitter and detected by the photodetector, and does not comprise an optical window; and replacing a used patient-contacting adhesive bandage layer of the used bandage-type medical sensor with a new patient-contacting adhesive bandage layer.

15. A method of remanufacturing a used bandage-type medical sensor, comprising:

obtaining the used bandage-type medical sensor, the used bandage-type medical sensor comprising an electrically conductive adhesive transfer tape (ECATT) layer disposed in a sensor body of the used bandage-type medical sensor and surrounding a detector of the used bandage-type medical sensor to shield the detector from EMI, wherein the ECATT layer is electrically insulated from external surfaces of the used bandage-type medical sensor; and replacing a used patient-contacting adhesive bandage layer of the used bandage-type medical sensor with a new patient-contacting insulative adhesive bandage layer.

* * * * *